(12) United States Patent
Choi et al.

(10) Patent No.: US 12,203,117 B2
(45) Date of Patent: Jan. 21, 2025

(54) METHOD OF PRODUCING SULFUR-CONTAINING AMINO ACID OR DERIVATIVE THEREOF

(71) Applicant: CJ CHEILJEDANG CORPORATION, Seoul (KR)

(72) Inventors: Sol Choi, Seoul (KR); Hee Ju Kim, Seoul (KR); Jin Ah Rho, Seoul (KR); Jin Nam Lee, Seoul (KR); Han Hyoung Lee, Seoul (KR); Sun Young Lee, Seoul (KR); Sang Jun Kim, Seoul (KR); Jihyun Shim, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 492 days.

(21) Appl. No.: 17/597,019

(22) PCT Filed: Jun. 26, 2020

(86) PCT No.: PCT/KR2020/008412
§ 371 (c)(1),
(2) Date: Dec. 22, 2021

(87) PCT Pub. No.: WO2020/263041
PCT Pub. Date: Dec. 30, 2020

(65) Prior Publication Data
US 2022/0315964 A1    Oct. 6, 2022

(30) Foreign Application Priority Data
Jun. 28, 2019  (KR) .................... 10-2019-0077998

(51) Int. Cl.
| C12P 13/12 | (2006.01) |
| C07K 14/245 | (2006.01) |
| C07K 14/34 | (2006.01) |
| C12N 15/70 | (2006.01) |
| C12N 15/77 | (2006.01) |

(52) U.S. Cl.
CPC ............ *C12P 13/12* (2013.01); *C07K 14/245* (2013.01); *C07K 14/34* (2013.01); *C12N 15/70* (2013.01); *C12N 15/77* (2013.01)

(58) Field of Classification Search
CPC ....... C12P 13/12; C07K 14/245; C07K 14/34; C12N 15/70; C12N 15/77; C12R 2001/19; C12R 2001/28
See application file for complete search history.

(56) References Cited

U.S. PATENT DOCUMENTS

| 7,662,943 B2 | 2/2010 | Park et al. |
| 9,109,242 B2 | 8/2015 | Park et al. |
| 10,273,491 B2 | 4/2019 | Lee et al. |
| 10,584,338 B2 | 3/2020 | Lee et al. |

| 2009/0298135 A1 | 12/2009 | Maier et al. |
| 2010/0317067 A1 | 12/2010 | Kim et al. |
| 2013/0183726 A1 | 7/2013 | Figge et al. |

FOREIGN PATENT DOCUMENTS

| EP | 1907559 A1 | 4/2008 |
| EP | 1724344 B1 | 2/2011 |
| KR | 10-2007-0036139 A | 4/2007 |
| KR | 10-2008-0028940 A | 4/2008 |

OTHER PUBLICATIONS

Caf19925, GenBank database. Feb. 27, 2015. (Year: 2015).*
Caf19926, GenBank database. Feb. 27, 2015. (Year: 2015).*
Caf19927, GenBank database. Feb. 27, 2015. (Year: 2015).*
Madden et al., KR20080028940A, English Translation (Espacenet). (Year: 2008).*
Ikeda M.et al., GeneBank WP_011014211.1, 2018 «NCBI GeneBank».
Ikeda M.et al., "GeneBank WP_011014212.1", 2018 «NCBI GeneBank».
Ikeda M.et al., "GeneBank WP_011014213.1", 2018 «NCBI GeneBank».
Bolten, Christoph J., Hartwig Schroder, Jeroen Dickschat, and Christoph Wittmann. Towards Methionine Overproduction in Corynebacterium glutamicum Methanethiol and Dimethyldisulfide as Reduced Sulfur Sources. J. Microbiol. Biotechnol. (2010), 20(8), 1196-1203.
C. Troschel et al., "Characterization of Methionine Export in *Corynebacterium glutamicum*", Journal of Bacteriology, pp. 3786-3794, Jun. 2005.
D. J. Koch, C. Ruckert, D. A. Rey, A. Mix, A. Puhler, J. Kalinowski. 2005. Role of the ssu and seu Genes of Corynebacterium glutamicum ATCC 13032 in Utilization of Sulfonates and Sulfonate Esters as Sulfur Sources. AEM. 71.10.6104-6114. 2005.
Eichhorn, Eric et al., 'Deletion analysis of the *Escherichia coli* taurine and alkanesulfonate transport systems', Journal of Bacteriology, 2000, 182, 10, 2687-2795.
Rey et al., "The putative transcriptional repressor McbR, member of the TetR-family, is involved in the regulation of the metabolic network direting the synthesis of sulfur containing amino acids in *Corynebacterium glutamicum*", J. Biotechnol. 103:51-65, 2003.
J. Sambrook et al., Molecular Cloning, A Laboratory Manual, 2nd Edition, Cold Spring Harbor laboratory press, Cold Spring Harbor, New York, 1989.
Kertesz, Michael A., 'Bacterial transporters for sulfate and organosulfur compounds', Research in Microbiology, 2001, 152, 279-290.
Pearson et al. "Improved tools for biological sequence comparison", (1988) Proc. Natl. Acad. Sci. USA 85, pp. 2444-2448.
Peyman, "Antisense Oligonucleotides: A New Therapeutic Principle", Chemical Reviews, 90:543-584 (1990).
Scheit, Nucleotide Analogs, John Wiley, New York (1980).
Sitnicka et al. Functional Analysis of Genes. Advances in Cell Biology. 2010, vol. 2.1-16, Sambrook et al. Molecular Cloning 2012, etc.

(Continued)

*Primary Examiner* — Yong D Pak
*Assistant Examiner* — Naghmeh Nina Moazzami
(74) *Attorney, Agent, or Firm* — Knobbe, Martens, Olson & Bear, LLP

(57) ABSTRACT

A method of producing sulfur-containing amino acids or derivatives of the sulfur-containing amino acids.

12 Claims, No Drawings
Specification includes a Sequence Listing.

(56) References Cited

OTHER PUBLICATIONS

Van der Rest et al., "A heat shock following electroporation induces highly efficient transformation of *Corynebacterium glutamicum* with xenogeneic plasmid DNA", Appl Microbiol Biotechnol 52:541-545, 1999.
Office Action in Russian Patent Application No. 2021139615, issued Feb. 15, 2023.
E.A. Bruford. "6.06.8 Bacterial Gene Nomenclature", *Comprehensive Biomedical Physics* (2014).
Demerec, et al. "A proposal for a uniform nomenclature in bacterial genetics" *Genetics* (1966) 54(1):61-76.

\* cited by examiner

METHOD OF PRODUCING SULFUR-CONTAINING AMINO ACID OR DERIVATIVE THEREOF

CROSS-REFERENCE TO RELATED APPLICATIONS

This application is the U.S. National Phase under 35 U.S.C. § 371 of International Application PCT/KR2020/008412, filed Jun. 26, 2020, which was published in Korean as WO 2020/263041 on Dec. 30, 2020, which claims priority to Korean Patent Application No. 10-2019-007798, filed Jun. 28, 2019, the entire content of which is incorporated herein by reference.

SEQUENCE LISTING STATEMENT

The present application contains a Sequence Listing, which is being submitted via EFS-Web on even date herewith. The Sequence Listing is submitted in a file entitled "Sequence_Listing_HAN030-010APC.txt," which was created on Dec. 22, 2021, and is approximately 44 kb in size. This Sequence Listing is hereby incorporated by reference.

TECHNICAL FIELD

The present disclosure relates to a method of producing sulfur-containing amino acids or derivatives of the sulfur-containing amino acids.

BACKGROUND ART

L-Amino acids have been industrially produced by way of fermentation methods using microorganisms belonging to the genus *Brevibacterium*, the genus *Corynebacterium*, the genus *Escherichia*, and the like. In such production methods, bacterial strains isolated from nature, artificial mutant strains thereof, or strains modified to have enhanced activity of an enzyme involved in L-amino acid biosynthesis via DNA recombination technology have been used.

Meanwhile, sulfur-containing amino acids have been used as ingredients for synthesis of animal feeds, food additives, pharmaceutically injectable fluids, and medicaments, and research has been conducted to biologically produce sulfur-containing amino acids and derivatives thereof.

For example, U.S. Patent Application Publication No. US 2009-0298135 A1 discloses that 0.8 g/L of L-methionine was produced by deleting metJ gene on the genome of *Escherichia coli* and over-expressing YjeH protein, which is an L-methionine exporter. Also, BrnF and BrnE polypeptides have been reported as L-methionine exporters of *Corynebacterium glutamicum* (C. Troschel et al., *Journal of Bacteriology*, pp. 3786-3794, June 2005).

Meanwhile, in the production of sulfur-containing amino acids, an amount of NADPH consumed in microorganisms may vary according to the reducing power of a sulfur source. For example, while sulfides that do not require NADPH have the highest theoretical yields, sulfates that require four NADPHs have low theoretical yields. However, sulfides are disadvantageous in that they have been known to cause cell damage and have low stability. Therefore, a high yield may be expected when using thiosulfate, which is a sulfur source having a low NADPH demand and high intracellular stability, in the production of sulfur-containing amino acids. However, while a membrane protein of *Escherichia coli* capable of using thiosulfate has been attested (J Bacteriol. 1995 July; 177 14)), a membrane protein of microorganisms belonging to the genus *Corynebacterium* capable of efficiently using thiosulfate has not been revealed in the art.

DISCLOSURE

Technical Problem

The present inventors have newly found that a protein encoded by ssuABC gene is involved in influx of thiosulfate of microorganisms and confirmed that a microorganism modified to have enhanced activity of the protein has enhanced ability to produce sulfur-containing amino acids using thiosulfate as a sulfur source, thereby completing the present disclosure.

Technical Solution

The present disclosure provides a method of producing a sulfur-containing amino acid and a derivative of the sulfur-containing amino acid, the method including culturing a genetically modified microorganism in a culture medium containing thiosulfate, wherein the microorganism includes genetic modification to increase activity of a protein encoded by ssuABC gene compared to a non-modified microorganism.

The present disclosure provides a microorganism producing a sulfur-containing amino acid or a derivative of the sulfur-containing amino acid and including genetic modification to increase activity of a protein encoded by ssuABC gene compared to a non-modified microorganism.

The present disclosure provides a composition for producing a sulfur-containing amino acid or a derivative of the sulfur-containing amino acid, wherein the composition includes: a microorganism including genetic modification to increase activity of a protein encoded by ssuABC gene compared to a non-modified microorganism, or a culture thereof; and thiosulfate.

The present disclosure provides a use of a protein encoded by ssuABC gene as a thiosulfate transporter.

The present disclosure provides a use of a microorganism including genetic modification to increase activity of a protein encoded by ssuABC gene compared to a non-modified microorganism for producing a sulfur-containing amino acid or a derivative of the sulfur-containing amino acid.

Advantageous Effects

Sulfur-containing amino acids or derivatives thereof may be mass-produced using the microorganism, the composition, the method of producing a sulfur-containing amino acid or sulfur-containing amino acid derivative thereof using the same according to the present disclosure, and thus may be efficiently used in production of useful products including the sulfur-containing amino acids or derivatives thereof.

BEST MODE

Each description and embodiment disclosed in the present disclosure may be applied to different descriptions and embodiments herein. In other words, all combinations of various components disclosed in the present disclosure are included within the scope of the present disclosure. Furthermore, the scope of the present disclosure should not be limited by the descriptions provided below.

Those skilled in the art will recognize or be able to ascertain, using no more than routine experimentation, many equivalents to specific embodiments of the present disclosure. Such equivalents are intended to be encompassed in the scope of the present disclosure.

An aspect of the present disclosure provides a method of producing a sulfur-containing amino acid and a derivative of the sulfur-containing amino acid, the method including culturing a genetically modified microorganism in a culture medium containing thiosulfate.

Another aspect of the present disclosure provides a genetically modified microorganism producing a sulfur-containing amino acid or a derivative of the sulfur-containing amino acid.

The microorganism may include genetic modification to increase activity of a protein encoded by ssuABC gene compared to the microorganism before the genetic modification.

The manufacturing method may include culturing a microorganism having enhanced activity of the protein encoded by the ssuABC gene compared to intrinsic activity in a thiosulfate-containing culture medium.

In an embodiment of the present disclosure, the method may be a method of increasing production of sulfur-containing amino acids or derivatives of the sulfur-containing amino acids by the microorganism.

The manufacturing method may include bringing the microorganism having enhanced activity of the protein encoded by ssuABC gene compared to intrinsic activity into contact with thiosulfate.

As used herein, the expression 'protein encoded by ssuABC gene' refers to a protein that the ssuABC gene encodes or a protein expressed by ssuABC gene and may also be referred to as 'SsuABC protein' (hereinafter referred to as "SsuABC protein"). Conventionally, SsuABC protein has been known to be involved in transport of aliphatic sulfonate. The protein is one type of ATP-binding cassette transporters (ABC transporters) and is known to be present in microorganisms such as *Escherichia coli, Bacillus clausii, Xanthomonas citri,* and *Corynebacterium glutamicum.* The SsuABC protein is a complex of SsuA, SsuB, and SsuC proteins, and SsuA is known as a periplasmic-binding protein. SsuB is known as a nucleotide-binding protein, and SsuC is known as an ABC transporter permease. However, it is not known whether the protein complex is involved in transport of thiosulfate rather than aliphatic sulfonate.

In the present disclosure, it has been newly revealed that the SsuABC protein is involved in transport of thiosulfate, and it was confirmed that production of a sulfur-containing amino acid may be increased by enhancing activity of any one of proteins selected from SsuA, SsuB, and SsuC which are components of the SsuABC protein.

The SsuABC protein of the present disclosure may be derived from a microorganism belonging to the genus *Corynebacterium,* but is not limited thereto.

Specifically, the SsuABC protein may be derived from *Corynebacterium glutamicum, Corynebacterium crudilactis, Corynebacterium crenatum, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris, Corynebacterium pacaense, Corynebacterium suranareeae,* or *Corynebacterium flavescens,* more specifically derived from *Corynebacterium glutamicum, Corynebacterium callunae, Corynebacterium deserti,* or *Corynebacterium suranareeae,* even more specifically derived from *Corynebacterium glutamicum,* without being limited thereto. An amino acid sequence derived from the SsuABC protein belonging to the genus *Corynebacterium* may be available from a known database such as GenBank of the National Center for Biotechnology Information (NCBI), without being limited thereto.

The SsuABC protein of the present disclosure may be interpreted as not only one or more proteins and/or protein complexes involved in thiosulfate transport, but also a system including the same as a component, that is, a thiosulfate transport system itself. That is, in a system in which one or more proteins interact to transport a substrate, the term "transporter" may be interpreted to include not only each protein but also two or more proteins or the entire system throughout the specification.

The SsuA, SsuB, and SsuC proteins constituting the SsuABC protein of the present disclosure may have amino acid sequences having at least 80% identity with amino acid sequences of SEQ ID NOS: 43, 44, and 45, respectively. Specifically, the SsuA, SsuB, and SsuC proteins may include amino acid sequences of SEQ ID NOS: 43, 44, and 45, respectively or may include amino acid sequences having at least 80%, 90%, 95%, 97%, or 99% homology or identity with the amino acid sequences of SEQ ID NOS: 43, 44, and 45, respectively. Also, it will be obvious that any protein having the amino acid sequences including deletion, modification, or addition of some amino acids is within the scope of the present disclosure as long as the amino acid sequences retain the above-described homology or identity and effects equivalents to those of the polypeptide (that is, activity to specifically transport thiosulfate among sulfur sources).

In addition, any polypeptide, having thiosulfate-specific transporter activity and encoded by a polynucleotide hybridized with a probe constructed using known gene sequences, e.g., a nucleotide sequence entirely or partially complementary to a polynucleotide under stringent conditions may also be included without limitation.

That is, in the present disclosure, although the expression "protein or polypeptide including an amino acid sequence of a predetermined SEQ ID NO", "protein or polypeptide consisting of an amino acid sequence of a predetermined SEQ ID NO" or "protein or polypeptide having an amino acid sequence of a predetermined SEQ ID NO" is used, it is obvious that any protein including deletion, modification, substitution, conservative substitution, or addition of one or several amino acids may be used in the present disclosure as long as the protein or polypeptide has activity identical or equivalent to that of the polypeptide consisting of the amino acid sequence of the SEQ ID NO. For example, addition of a sequence not changing the function of the protein to the N-terminus and/or the C-terminus of the amino acid sequence, a naturally occurring mutation, a silent mutation thereof, or a conservative substitution thereof may be used.

As used herein, the term "conservative substitution" refers to substitution of one amino acid with a different amino acid having similar structural and/or chemical properties. Such amino acid substitution may generally occur based on similarity of polarity, charge, solubility, hydrophobicity, hydrophilicity, and/or amphipathic nature of a residue.

In an embodiment of the present disclosure, the ssuABC gene may include a nucleotide sequence have at least 80%, 85%, 90%, 95%, 96%, 97%, 98%, 99%, or 100% homology with the nucleotide sequence of SEQ ID NO: 8. Specifically, the ssuABC gene may consist of a nucleotide sequence having at least 80%, 85%, 90%, 95%, 96%, 97%, 98%, 99%, or 100% homology with the nucleotide sequence of SEQ ID NO: 8, without being limited thereto.

As used herein, the term "polynucleotide" has an inclusive meaning including DNA and RNA molecules, and a nucleotide that is a basic structural unit in the polynucleotide may include not only a natural nucleotide but also an analogue in which a sugar or a base is modified (Scheit, Nucleotide Analogs, John Wiley, New York (1980); Uhlman and Peyman, Chemical Reviews, 90:543-584 (1990)).

The polynucleotide may be a polynucleotide (ssuABC gene) encoding the SsuABC protein of the present disclosure. The polynucleotide of the present disclosure may include various modifications made in a coding region provided not to change the amino acid sequence of the polypeptide expressed from the coding region due to codon degeneracy or in consideration of codons preferred by a living organism in which the protein is expressed. The polynucleotide of the present disclosure may be, for example, a polynucleotide encoding a polypeptide having at least 80%, 85%, 90%, 95%, 96%, 97%, 98%, 99%, or 100% homology with the SsuABC protein of the present disclosure. Specifically, for example, polynucleotides encoding proteins including amino acid sequences having at least 80% of identity with the amino acid sequences of SEQ ID NOS: 43, 44, and 45, respectively, may be polynucleotides having at least 80%, 85%, 90%, 95%, 96%, 97%, 98%, 99%, or 100% homology or identity with a part of the nucleotide sequence of SEQ ID NO: 8. Specifically, the polynucleotides encoding proteins including amino acid sequences having at least 80% of identity with the amino acid sequences of SEQ ID NOS: 43, 44, and 45, respectively, may be polynucleotides having at least 80%, 85%, 90%, 95%, 96%, 97%, 98%, 99%, or 100% homology or identity with at least one selected from the group consisting a polynucleotide including $2530^{th}$ to $3489^{th}$ nucleotides, a polynucleotide including $1789^{th}$ to $2520^{th}$ nucleotides, and a polynucleotide including $1004^{th}$ to $1774^{th}$ nucleotides in the nucleotide sequence of SEQ ID NO: 8, without being limited thereto.

In addition, it is obvious that any polynucleotide that may be translated into a protein including an amino acid sequence having at least 80% identity with at least one amino acid sequence selected from the group consisting of SEQ ID NOS: 43, 44, and 45 due to codon degeneracy or a protein having homology or identity therewith may also be included. Alternatively, any polynucleotide encoding a protein including an amino acid sequence having at least 80% identity with at least one amino acid sequence selected from the group consisting of SEQ ID NOS: 43, 44, and 45 and hybridized with a probe constructed using known gene sequences, e.g., a nucleotide sequence entirely or partially complementary to the polynucleotide sequence under stringent conditions may be included without limitation. The term "stringent conditions" means conditions allowing specific hybridization between polynucleotides. Such conditions are disclosed in detail in known documents (For example, J. Sambrook et al., *Molecular Cloning, A Laboratory Manual*, 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York). For example, the stringent conditions may include performing hybridization between genes having a high homology or identity, e.g., a homology or identity of 70% or more, 80% or more, 85% or more, specifically 90% or more, more specifically 95% or more, even more specifically 97% or more, or most specifically 99% or more, without performing hybridization between genes having a homology or identity lower than the above homologies or identities, or washing once, specifically twice or three times, under conventional washing conditions for Southern hybridization at a salt concentration and temperature of 60° C., 1×SSC, and 0.1% SDS, specifically 60° C., 0.1×SSC, 0.1% SDS, and more specifically 68° C., 0.1×SSC, and 0.1% SDS.

Hybridization requires that two polynucleotides have complementary sequences, although bases mismatch according to the degree of stringency of hybridization. The term "complementary" is used to describe the relationship between bases of nucleotides capable of hybridizing with each other. For example, with respect to DNA, adenosine is complementary to thymine and cytosine is complementary to guanine. Thus, the present disclosure may include not only a substantially similar nucleotide sequence but also a polynucleotide fragment isolated but complementary to the entire sequence.

Specifically, the polynucleotides having homology or identity with the polynucleotide of the present disclosure may be detected using hybridization conditions including a hybridization process performed at a $T_m$ value of 55° C. and the above-described conditions. Also, the $T_m$ value may be, but is not limited to, 60° C., 63° C., or 65° C., and may be appropriately adjusted by those skilled in the art according to intended purposes.

An appropriate degree of stringency for hybridization of the polynucleotides may depend on lengths and a degree of complementarity of the polynucleotides and parameters thereof are well known in the art (Sambrook et al., supra, 9.50-9.51, 11.7-11.8).

As used herein, the term "homology" or "identity" refers to a degree of relatedness between two amino acid sequences or nucleotide sequences and may be expressed as a percentage. The terms homology and identity may often be used interchangeably.

Sequence homology or identity of conserved polynucleotides or polypeptides may be determined by standard alignment algorithm and default gap penalties established by a program may be used together therewith. Substantially, homologous or identical sequences may hybridize with each other at least about 50%, 60%, 70%, 80%, or 90% of the entire sequence or the entire length under moderate or highly stringent conditions. It is obvious that polynucleotides including a general codon or degenerate codon may also be considered in hybridization.

The homology, similarity, or identity between two polynucleotide or polypeptide sequences may be determined using any computer algorithm known in the art, e.g., "FASTA" program, using default parameters introduced by Pearson et al. (1988) *Proc. Natl. Acad. Sci. USA* 85:2444. Alternatively, the homology, similarity, or identity may be determined using the Needleman-Wunsch algorithm (Needleman and Wunsch, 1970, *J. Mol. Biol.* 48:443-453) as implemented in the Needleman program of the EMBOSS package (EMBOSS: The European Molecular Biology Open Software Suite, Rice et al., 2000, *Trends Genet.* 16:276-277) (version 5.0.0 or later) (including GCG program package (Devereux, J. et al., *Nucleic Acids Research* 12:387 (1984)), BLASTP, BLASTN, FASTA (Atschul, S. F., et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST, from the National Center for Biotechnology Information database, or ClustalW.

The homology, similarity, or identity between polynucleotides or polypeptides may be determined by comparing sequence information using a GAP computer program as introduced by Needleman et al., (1970), *J Mol Biol.* 48:443 as disclosed by Smith and Waterman, *Adv. Appl. Math*

(1981) 2:482. Briefly, the GAP program defines similarity as the number of aligned symbols (i.e., nucleotides or amino acids) which are similar, divided by the total number of symbols in a shorter of two sequences. Default parameters for the GAP program may include: (1) a binary comparison matrix (containing a value of 1 for identities and 0 for non identifies) and the weighted comparison matrix of Gribskov et al. (1986), *Nucl. Acids Res.* 14:6745 as described by Schwartz and Dayhoff, eds., *Atlas Of Protein Sequence and Structure*, National Biomedical Research Foundation, pp. 353-358 (1979) (or EDNAFULL (EMBOSS version of NCBI NUC4.4) substitution matrix); (2) a penalty of 3.0 for each gap and an additional penalty of 0.10 for each symbol in each gap (or a gap open penalty of 10 and a gap extension penalty of 0.5); and (3) no penalty for end gaps.

Also, the sequence homology, similarity, or identity between two given polynucleotides or polypeptides may be identified by comparing sequences thereof by southern hybridization under defined stringent conditions, and the defined stringent hybridization conditions are within the scope of the technology and may be defined by a method well known to one of ordinary skill in the art (For example, J. Sambrook et al., *Molecular Cloning, A Laboratory Manual*, 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York).

As used herein, the term "enhancement" of the activity of the polypeptide or protein refers to an increase in the activity of the polypeptide compared to intrinsic activity. The enhancement may be used interchangeably with up-regulation, overexpression, increase, and the like.

In this regard, the increase may include all of those exhibiting activity that was not originally possessed or exhibiting enhanced activity compared to intrinsic activity or activity before modification. The "intrinsic activity" refers to activity of a particular polypeptide or protein originally possessed by a parent strain or non-modified microorganism before transformation when the microorganism is transformed by genetic modification caused by a natural or artificial factor. This term may be used interchangeably with "activity before modification". The "enhancement" or "increase" of activity of a polypeptide or protein compared to intrinsic activity means that activity of a particular polypeptide or protein is improved compared to that originally possessed by a parent strain or non-modified microorganism before transformation.

The term "increase in activity" may be achieved by introduction of a foreign polypeptide or protein or enhancement of activity of an endogenous polypeptide or protein, specifically achieved by enhancement of activity of an endogenous polypeptide or protein. The enhancement of activity of the polypeptide or protein may be identified based on an increase in a degree of activity of the polypeptide or protein, an expression level thereof, or an amount of a product released therefrom.

As used herein, the expression "enhancement or increase of activity of a protein encoded by ssuABC gene or SsuABC protein" may also be referred to as "genetic modification to increase activity of a protein encoded by ssuABC gene", and this means that the activity of at least one protein selected from the group consisting of SsuA, SsuB, and SsuC proteins constituting the SsuABC protein is enhanced compared to intrinsic activity.

The increase in activity of the SsuABC protein may include increase in the activity by both introduction of at least one protein selected from the group consisting of foreign SsuA, SsuB, and SsuC proteins and enhancement of activity of at least one protein selected from the group consisting of endogenous SsuA, SsuB, and SsuC proteins.

As used herein, the term "introduction of a protein" refers to providing activity of a particular protein to a microorganism which does not originally possess the protein or enhancing the activity of the protein compared to the intrinsic activity of the protein or the activity before modification. For example, the introduction of a protein may refer to introduction of a particular protein, introduction of a polynucleotide encoding a particular protein into a chromosome of the microorganism, or introduction of a vector including a polynucleotide encoding a particular protein into a microorganism, thereby expressing the activity of the protein.

Enhancement of the activity of the polypeptide or protein may be achieved by applying various methods well known in the art without limitation, as long as the activity of a target polypeptide or protein is enhanced compared to that of the microorganism before modification. Specifically, any genetic engineering and/or protein engineering methods well known in the art as common methods of the molecular biology may be used, without being limited thereto (Sitnicka et al. Functional Analysis of Genes. *Advances in Cell Biology.* 2010, Vol. 2.1-16, Sambrook et al. *Molecular Cloning* 2012, etc.).

Specifically, in the present disclosure, the enhancement of the activity may be achieved by:
 (1) increasing a copy number of a gene or polynucleotide encoding the polypeptide or protein in a cell;
 (2) replacing a gene expression regulatory region on the chromosome encoding the polypeptide or protein with a sequence with stronger activity;
 (3) modifying a base sequence encoding an initiation codon or a 5'-UTR region of the polypeptide or protein;
 (4) modifying a nucleotide sequence on the chromosome to enhance the activity of the polypeptide or protein;
 (5) introducing a foreign polynucleotide having the activity of the polypeptide or protein or a codon optimized variant polynucleotide of the polynucleotide; or
 (6) modification to enhance the activity via any combination of the above-described methods, without being limited thereto.

The method of enhancing activity of a polypeptide or protein by the protein engineering method may be performed by modifying or chemically modifying an exposed region selected by analyzing a three-dimensional structure of the polypeptide or protein, without being limited thereto.

The increasing of the copy number of the gene or polynucleotide encoding the polypeptide or protein described in (1) above may be performed by any method well known in the art, e.g., by introducing a vector, which replicates and functions irrespective of a host cell and is operably linked to the gene or polynucleotide encoding the polypeptide or protein, into a host cell. Alternatively, the increasing of the copy number may be performed by introducing a vector, which is operably linked to the gene and is capable of inserting the gene or polynucleotide into the chromosome of the host cell, into the host cell, but is not limited thereto.

The replacing of the gene expression regulatory region (or expression regulatory sequence) on the chromosome encoding the polypeptide or protein with a sequence with stronger activity described in (2) above may be performed by any method known in the art, e.g., by inducing mutation in the sequence by deletion, insertion, non-conservative or conservative substitution, or any combination thereof or by replacing the sequence with a sequence with stronger activity, to further enhance the activity of the expression regulatory region. The expression regulatory region may include a promoter, an operator sequence, a ribosome-binding site-encoding sequence, and a sequence for regulating termination of transcription and translation, without being limited thereto. For example, the method may be performed by linking a stronger heterologous promoter instead of an intrinsic promoter, without being limited thereto.

Examples of the stronger promoter known in the art may include cj1 to cj7 promoters (U.S. Pat. No. 7,662,943 B2), lac promoter, trp promoter, trc promoter, tac promoter, Lambda phage PR promoter, PL promoter, tet promoter, lysCP1 promoter (US 2010-0317067 A1), spl1 promoter, spl7 promoter, spl13 promoter (U.S. Ser. No. 10/584,338 B2), gapA promoter, EF-Tu promoter, groEL promoter, aceA or aceB promoter, O2 promoter (U.S. Pat. No. 10,273,491 B2), tkt promoter, and yccA promoter, without being limited thereto.

The modifying of the base sequence encoding an initiation codon or a 5'-UTR region of the polypeptide or protein described in (3) above may be performed by any method known in the art, e.g., by substituting an intrinsic initiation codon with another initiation codon with a higher expression level of the polypeptide or protein, without being limited thereto.

The modifying the nucleotide sequence on the chromosome to enhance the activity of the polypeptide or protein described in (4) above may be performed by any method known in the art, e.g., by inducing modification on an expression regulatory sequence by deletion, insertion, non-conservative or conservative substitution, or any combination thereof to further enhance the activity of the nucleotide sequence or replacing the sequence with a nucleotide sequence modified to have stronger activity. The replacing may be insertion of the gene into the chromosome by homologous recombination, without being limited thereto. A vector used herein may further include a selection marker to detect the chromosomal insertion.

The introducing of the foreign polynucleotide having the activity of the polypeptide or protein described in (5) above may be performed by any method known in the art, e.g., by introducing a foreign polynucleotide encoding a polypeptide or protein having activity identical/similar to that of the polypeptide or protein, or introducing a codon optimized variant polynucleotide thereof into a host cell. The origin or sequence of the foreign polynucleotide is not particularly limited as long as the foreign polynucleotide exhibits activity identical/similar to that of the polypeptide or protein. In addition, a foreign polynucleotide codon-optimized for optimized transcription and translation in the host cell may be introduced into the host cell. The introduction may be performed by any known transformation method appropriately selected by those of ordinary skill in the art. As the introduced polynucleotide is expressed in the host cell, the polypeptide or protein is produced, thereby increasing the activity thereof.

Finally, the combination of the above-described methods described in (6) may be performed by applying one or more methods described in (1) to (5).

The enhancement of the activity of the polypeptide or protein as described above may be an increase in the activity or concentration of the polypeptide or protein compared with the activity or concentration of the polypeptide or protein expressed in wild-type or non-modified microorganism strains or an increase in an amount of a product obtained from the polypeptide or protein, without being limited thereto.

As used herein, the term "strain before modification" or "microorganism before modification" does not exclude strains including mutations naturally occurring in microorganisms and may refer to a wild-type strain or natural-type strain, or a strain before being transformed by genetic modification due to a natural or artificial factor. The "strain before modification" or "microorganism before modification" may be used interchangeably with "non-mutated strain", "non-modified strain", "non-mutated microorganism", "non-modified microorganism", or "reference microorganism".

As used herein, the term "vector" refers to a DNA construct containing a nucleotide sequence of a polynucleotide encoding a target protein and operably linked to a suitable regulatory sequence so as to be able to express the target protein in a suitable host cell. The regulatory sequence may include a promoter capable of initiating transcription, any operator sequence for regulating the transcription, a sequence encoding a suitable mRNA ribosome binding site, and a sequence for regulating termination of transcription and translation. When a suitable host cell is transformed with the vector, the vector may replicate or function independently from the host genome, or may integrate into genome thereof. For example, a polynucleotide encoding a target protein may be inserted into the chromosome by using a vector for chromosomal insertion into cells. The insertion of the polynucleotide into the chromosome may be performed by any method known in the art, for example, homologous recombination, but is not limited thereto. The vector may further include a selection marker to detect chromosomal insertion. The selection marker is used to select cells that are transformed with the vector, that is, to confirm insertion of desired nucleic acid molecules, and examples of the selection marker may include markers providing selectable phenotypes, such as drug tolerance, nutrient requirement, resistance to cytotoxic agents, or expression of surface polypeptide. Only cells expressing the selection marker are able to survive or to show different phenotypes under the environment treated with a selective agent, and thus the transformed cells may be selected.

The vector used in the present disclosure is not particularly limited, and any vector known in the art may be used. Examples of vectors commonly used in the art may include a natural or recombinant plasmid, cosmid, virus and bacteriophage. For example, pWE15, M13, MBL3, MBL4, IXII, ASHII, APII, t10, t11, Charon4A, and Charon21A may be used as the phage vector or the cosmid vector. As the plasmid vector, pBR type, pUC type, pBluescriptII type, pGEM type, pTZ type, pCL type, and pET type may be used. Specifically, pDZ, pACYC177, pACYC184, pCL, pECCG117, pUC19, pBR322, pMW118, and pCC1 BAC may be used. However, the embodiment is not limited thereto.

As used herein, the term "transformation" refers to a process of introducing a vector including a polynucleotide encoding a target protein into a host cell or microorganism in such a way that the polypeptide encoded by the polynucleotide is expressed in the host cell. The transformed polynucleotide may be either in a form inserted into the chromosome of the host cell or in a form located outside the chromosome as long as the protein is expressed in the host cell. In addition, the polynucleotide includes DNA and/or RNA encoding the target protein. The polynucleotide may be introduced into the host cell in any form as long as the polynucleotide is introduced into the host cell and the polypeptide is expressed therein. For example, the polynucleotide may be introduced into the host cell in the form of an expression cassette that is a gene construct including all of the essential elements required for self-replication. The expression cassette may generally include a promoter operably linked to the polynucleotide, a transcription termination signal, a ribosome-binding site, and a translation termination signal. The expression cassette may be in the form of a self-replicable expression vector. Also, the polynucleotide may be introduced into the host cell in its original form and operably linked to a sequence required for the expression in the host cell, without being limited thereto.

In addition, as used herein, the term "operably linked" refers to an operable linkage between a promoter sequence, which enables initiation and mediation of transcription of a polynucleotide encoding the target protein of the present disclosure, and the gene sequence.

Methods for the transformation with the vector according to the present disclosure include any methods enabling introduction of a nucleic acid into a host cell and may be performed by suitable standard techniques well known in the art selected in accordance with the host cell. For example, electroporation, calcium phosphate ($CaPO_4$) precipitation, calcium chloride ($CaCl_2$) precipitation, microinjection, polyethylene glycol (PEG) method, DEAE-dextran method, cationic liposome method, and lithium acetate-DMSO method may be used, but the present disclosure is not limited thereto.

The microorganism of the present disclosure may include both wild-type microorganisms and microorganisms including natural or artificial genetic modification, and any microorganism introduced with or including a thiosulfate transporter according to the present disclosure may be included therein without limitation.

The microorganism of the present disclosure may include: at least one of the thiosulfate transporter of the present disclosure; a polynucleotide encoding the same; and a vector including the polynucleotide.

The microorganism may be a microorganism producing L-amino acids and/or derivatives thereof.

As used herein, the term "microorganism producing L-amino acids and/or derivatives thereof" includes both a microorganism naturally having the ability to produce L-amino acids/derivatives thereof and a microorganism prepared by providing the ability to produce L-amino acids/derivatives thereof to a parent strain unable to produce the L-amino acids or derivatives thereof. Specifically, any microorganism including genetic modification to produce a target L-amino acid or derivatives thereof by having a particular mechanism weakened or enhanced via introduction of an exogenous gene or enhancement or inactivation of activity of an endogenous gene.

For example, the microorganism may be a microorganism in which a biosynthesis pathway of an L-amino acid is enhanced or a degradation pathway thereof is weakened. For example, the L-amino acid-producing microorganism may be a microorganism in which an L-methionine biosynthesis pathway is enhanced.

For example, the microorganism may be a microorganism in which activity of methionine and cysteine biosynthesis repressor (McbR) protein or MetJ protein is weakened or eliminated or a microorganism in which the methionine producing ability is enhanced and/or added by enhancing activity of methionine synthase (MetH) or sulfite reductase (CysI). Alternatively, the microorganism may be a microorganism in which expression of a gene encoding an enzyme involved in the L-amino acid biosynthesis pathway is enhanced or an enzyme involved in the L-amino acid degradation pathway is inactivated.

Specifically, examples of proteins or genes whose expression may be controlled to enhance the biosynthesis pathway of L-amino acids or weaken/inactivate the degradation pathway thereof are as follows. They are provided in the order of a protein, a representative gene encoding the protein, and a representative EC number thereof. A first letter of the protein is written by a capital letter and the gene is written using italic font. For example, thiosulfate sulfurtransferase such as Rdl2p, GlpE, PspE, YgaP, ThiI, YbbB, SseA, YnjE, YceA, YibN, NCgl0671, NCgl1369, NCgl2616, NCgl0053, NCgl0054, NCG12678, and NCgl2890; sulfite reductase, cysI; thiosulfate/sulphate transport system, cysPUWA (EC 3.6.3.25); 3'-phosphoadenosine 5'-phosphosulphate reductase, cysH (EC 1.8.4.8); sulfite reductase, cysJI (EC 1.8.1.2); cysteine synthase A, cysK (EC 2.5.1.47); cysteine synthase B, cysM (EC 2.5.1.47); serine acetyltransferase, cysE (EC 2.3.1.30); glycine cleavage system, gcvTHP-lpd (EC 2.1.2.10, EC 1.4.4.2, EC 1.8.1.4); lipoyl synthase, lipA (EC 2.8.1.8); lipoyl protein ligase, lipB (EC 2.3.1.181); phosphoglycerate dehydrogenase, serA (EC 1.1.1.95); 3-phosphoserine phosphatase, serB (EC 3.1.3.3); 3-phosphoserine/phosphohydroxythreonine aminotransferase, serC (EC 2.6.1.52); serine hydroxymethyltransferase, glyA (EC 2.1.2.1); aspartokinase I (EC 2.7.2.4); homoserine dehydrogenase I, thrA (EC 1.1.1.3); aspartate kinase, lysC (EC 2.7.2.4); homoserine dehydrogenase, hom (EC 1.1.1.3); homoserine O-acetyltransferase, metX (EC 2.3.1.31); homoserine O-succinyltransferase, metA (EC 2.3.1.46); cystathionine gamma-synthase, metB (EC 2.5.1.48); β-C-S-lyase, aecD (EC 4.4.1.8, beta-lyase); cystathionine beta-lyase, metC (EC 4.4.1.8); B12-independent homocysteine S-methyltransferase, metE (EC 2.1.1.14); methionine synthase, metH (EC 2.1.1.13); methylenetetrahydrofolate reductase, metF (EC 1.5.1.20); L-methionine exporter BrnFE; valine exporter YgaZH (B2682, B2683), ygaZH (b2682, b2683); exporter YjeH, b4141; pyridine nucleotide transhydrogenase PntAB, pntAB (EC 1.6.1.2); O-succinylhomoserine sulfhydrylase, MetZ (EC 2.5.1.48); and phosphoenolpyruvate carboxylase, Pyc (EC 4.1.1.31) may be used. The biosynthesis pathway of L-amino acids may be enhanced, or the degradation pathway thereof may be weakened by enhancing the activity of one or more proteins described above or some proteins constituting the system or by overexpressing polynucleotides encoding the same. Alternatively, among glucose 6-phosphate isomerase, pgi (EC 5.3.1.9); homoserine kinase, thrB (EC 2.7.1.39); S-adenosylmethionine synthase, metK (EC 2.5.1.6); dihydrodipicolinate synthase, dapA (EC 4.2.1.52); phosphoenolpyruvate carboxylkinase, pck (EC 4.1.1.49); formyltetrahydrofolate hydrolase, purU (EC 3.5.1.10); pyruvate kinase I, pykF (EC 2.7.1.40); pyruvate kinase II, pykA (EC 2.7.1.40); cystathionine γ-lyase, cg3086 (EC 4.4.1.1); cystathionine β-synthase, cg2344 (EC 4.2.1.22); regulatory protein Cg3031, cg3031; methionine and cysteine biosynthesis repressor protein McbR, mcbR; Met transcriptional repressor protein, metJ; L-methionine transporter MetQNI, metQ, metN, metI; N-acyltransferase, yncA; sRNA fnrS; and L-methionine transporter, metP, at least one protein selected therefrom may be inactivated or weakened or expression of the gene encoding the protein may be suppressed or removed.

However, these are merely examples, and the microorganism may be a microorganism in which expression of a gene encoding an enzyme involved in various known L-amino acid biosynthesis pathways is enhanced or an enzyme involved in degradation pathways are inactivated/weakened. The enhancement of activity of protein and increase in gene expression are as described above.

As used herein, the term "inactivation" or "weakening" of a polypeptide or protein is a concept including both reduction and elimination of the activity compared to intrinsic activity. The inactivation or weakening may be used interchangeably with down-regulation, decrease, and reduce. The inactivation or weakening may include a case in which activity of the protein is reduced or eliminated compared to intrinsic activity of the microorganism by mutation of a gene encoding the protein, modification of an expression regulatory sequence, or deletion of the gene in whole or in part, a case in which the overall activity of the protein in a cell is lower than that of native strains or non-modified strains due to inhibition of expression or translation of the gene encoding the same, a case in which the gene is not expressed, and a case in which no activity is obtained although the gene is expressed.

In the present disclosure, the inactivation/weakening of a protein may be achieved by various methods well known in the art, without being limited thereto (Nakashima N. et al., Bacterial cellular engineering by genome editing and gene silencing. *Int J Mol Sci.* 2014; 15(2):2773-2793, Sambrook et al. *Molecular Cloning* 2012, etc.).

Examples of the methods include
(1) deletion of the gene encoding the protein in whole or in part,
(2) modification of an expression regulatory region (or expression regulatory sequence) to reduce expression of the gene encoding the protein,
(3) modification of the gene sequence encoding the protein to eliminate or weaken the activity of the protein,
(4) introduction of an antisense oligonucleotide (e.g., introduction of antisense RNA) complementarily binding to a gene transcript encoding the protein,
(5) addition of a sequence complementary to a Shine-Dalgarno sequence of the gene encoding the protein upstream of the Shine-Dalgarno sequence to form a secondary structure preventing a ribosome from binding thereto,
(6) addition of a promotor for reverse transcription to the 3' terminus of the open reading frame (ORF) of a nucleotide sequence of the gene encoding the protein (Reverse transcription engineering, RTE), or any combination thereof, without being limited thereto.

Specifically, the deletion of the gene encoding the protein in whole or in part may be performed by replacing a polynucleotide encoding an intrinsic target protein in the chromosome with a polynucleotide having some deleted nucleotides or a marker gene using a vector for chromosomal insertion in the microorganism. As an example of deleting the polynucleotide in whole or in part, a method of deleting the polynucleotide by homologous recombination may be used, without being limited thereto.

In addition, the deletion of the gene in whole or in part may be performed by inducing mutation using light such as UV light or a chemical substance, and selecting strains from which the target gene is deleted from mutants. The deletion of the gene may include a method by DNA recombination technology. The DNA recombination technology may be performed by inducing homologous recombination by inserting a nucleotide sequence or vector having homology with the target gene into the microorganism. In addition, the inserted nucleotide sequence or vector may include a dominant selection marker, without being limited thereto.

In addition, the modification of the expression regulatory sequence may be achieved by applying various methods well known in the art. For example, the modification may be performed by inducing mutation in the expression regulatory region (expression regulatory sequence) by deletion, insertion, non-conservative or conservative substitution, or any combination thereof to further reduce the activity of the expression regulatory region (expression regulatory sequence) or by replacing the sequence with a sequence having weaker activity. The expression regulatory region may include a promoter, an operator sequence, a ribosome-binding site-encoding sequence, and a sequence for regulating termination of transcription and translation, without being limited thereto.

Also, the modification of the gene sequence may be performed by inducing mutation in the gene sequence by deletion, insertion, non-conservative or conservative substitution, or any combination thereof to further weaken the activity of the polypeptide or by replacing the sequence with a gene sequence modified to have weaker activity or a gene sequence modified not to have the activity, without being limited thereto.

For example, expression of the gene may be suppressed or weakened by forming a termination codon by introducing a mutation into the gene sequence.

However, the above-described methods are merely examples and those of ordinary skill in that art may prepare a microorganism producing L-amino acids and/or derivatives thereof using any method known in the art.

The L-amino acid and/or a derivative thereof may be a sulfur-containing amino acid and/or a derivative of the sulfur-containing amino acid.

As used herein, the term "sulfur-containing amino acid" or "derivative of the sulfur-containing amino acid" refers to an amino acid including sulfur or a derivative thereof, specifically one selected from methionine, cysteine, cystine, lanthionine, homocysteine, homocystine, homolanthionine, and taurine, but is not limited thereto, any amino acid including sulfur and derivatives thereof may be included within the scope of the present disclosure without limitation.

The microorganism of the present disclosure may be a microorganism belonging to the genus *Corynebacterium* sp., the genus *Escherichia* sp., or the genus *Lactobacillus* sp., without being limited thereto. The microorganism may include any microorganism having enhanced ability to produce L-amino acids and/or derivatives thereof by enhancing activity of an endogenous SsuABC protein or introducing a foreign SsuABC protein, without limitation.

The "microorganism belonging to the genus *Corynebacterium*" may include all microorganisms belonging to the genus *Corynebacterium*. Specifically, the microorganism may be *Corynebacterium glutamicum, Corynebacterium crudilactis, Corynebacterium crenatum, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris,* or *Corynebacterium flavescens*, and more specifically *Corynebacterium glutamicum, Corynebacterium stationis, Corynebacterium ammoniagenes, Corynebacterium callunae,* or *Corynebacterium deserti,* even more specifically *Corynebacterium glutamicum,* but is not limited thereto.

The "microorganism belonging to the genus *Escherichia*" may include all microorganisms belonging to the genus *Escherichia*. Specifically, the microorganism may be *Escherichia coli,* but is not limited thereto.

The microorganism of the present disclosure may be any microorganism including the thiosulfate transporter of the present disclosure and using thiosulfate as a sulfur source.

The production method of the present disclosure may include culturing the microorganism of the present disclosure in a culture medium containing thiosulfate.

As used herein, the term "culturing" refers to growing the microorganism in an appropriately adjusted environment. A culture process of the present disclosure may be performed according to an appropriate medium and culturing conditions known in the art. The culture process may be easily adjusted for use by a skilled person in the art according to a strain to be selected. The culturing of the microorganism may be performed in in a batch process, a continuous process, a fed-batch process, etc. known in the art, without being limited thereto.

As used herein, the term "culture medium" refers to a material in which nutrients required for culturing the microorganism are mixed as main ingredients and supplies nutrients and growth factors as well as water which are essential for survival and growth. Specifically, although culture media and other culturing conditions for culturing the microorganism of the present disclosure are not particularly limited as long as the culture media are commonly used in culturing microorganisms, the microorganism of the present disclosure may be cultured in an ordinary medium containing appropriate carbon sources, nitrogen sources, phosphorus sources, inorganic compounds, amino acids, and/or vitamins under aerobic conditions while adjusting temperature, pH, and the like.

In the present disclosure, the carbon sources may include carbohydrates such as glucose, saccharose, lactose, fructose, sucrose and maltose; sugar alcohols such as mannitol and sorbitol; organic acids such as pyruvic acid, lactic acid, and citric acid; and amino acids such as glutamic acid, methionine, and lysine. In addition, natural organic nutrients such as starch hydrolysates, molasses, blackstrap molasses, rice bran, cassava, sugar cane bagasse, and corn steep liquor may be used, and specifically carbohydrates such as glucose and sterile pretreated molasses (i.e., molasses converted to reduced sugars) may be used, and suitable amounts of any other carbon sources may also be used without limitation. These carbon sources may be used alone or in combination of at least two thereof, but are not limited thereto.

The nitrogen sources may include inorganic nitrogen sources such as ammonia, ammonium sulfate, ammonium chloride, ammonium acetate, ammonium phosphate, ammonium carbonate, and ammonium nitrate; and organic nitrogen sources such as amino acids, e.g., glutamic acid, methionine, and glutamine, peptone, NZ-amine, meat extract, yeast extract, malt extract, corn steep liquor, casein hydrolysate, fish or degradation products thereof, and defatted soybean cake or degradation products thereof. These nitrogen sources may be used alone or in combination of at least two thereof, without being limited thereto.

The phosphorus sources may include monopotassium phosphate, dipotassium phosphate, or sodium-containing salts corresponding thereto. As inorganic compounds, sodium chloride, calcium chloride, iron chloride, magnesium sulfate, iron sulfate, manganese sulfate, calcium carbonate, and the like may be used. Also, amino acids, vitamins, and/or appropriate precursors may further be included. These components and precursors may be added to the culture medium in a batch or continuous process, without being limited thereto.

Also, during the culturing process of the microorganism, compounds such as ammonium hydroxide, potassium hydroxide, ammonia, phosphoric acid, and sulfuric acid may be added to the culture medium in a proper method to adjust the pH of the culture medium. Also, a defoaming agent such as fatty acid polyglycol ester may be added during culturing in order to inhibit formation of foams. In addition, oxygen or oxygen-containing gas may be injected into the culture medium to maintain the culture medium in an aerobic condition, or nitrogen, hydrogen, or carbon dioxide gas may be injected into the culture medium to maintain the culture medium in anaerobic and micro-aerobic conditions without injecting any other gases therefor, but the embodiment is not limited thereto.

The temperature of the culture medium may be maintained at 25° C. to 40° C., more specifically at 30° C. to 37° C., without being limited thereto. The culturing may be continued until a desired amount of a product is obtained, for example, for 0.5 hours to 60 hours, without being limited thereto.

The term "sulfur source" of the present disclosure may be used interchangeably with "source supplying sulfur" and refers to a sulfur-containing substance available in production of a sulfur-containing amino acid.

In culturing the microorganism, the sulfur source may be an important factor in determining a metabolic pathway in the microorganism. However, factors involved in transport of various sulfur sources and factors involved in degradation thereof have not been accurately revealed. For example, although it has been known that wild-type *Corynebacterium glutamicum* use various sulfur sources, it is known that the SsuABC protein is not involved in transport of sulfate or sulfite but involved only in transport of aliphatic sulfonate (D. J. Koch, C. Ruckert, D. A. Rey, A. Mix, A. Puhler, J. Kalinowski. 2005. Role of the ssu and seu Genes of *Corynebacterium glutamicum* ATCC 13032 in Utilization of Sulfonates and Sulfonate Esters as Sulfur Sources. AEM. 71.10.6104-6114. 2005). That is, a protein transporting the sulfur source into a cell has substrate specificity. In addition, after the sulfur source is transported into the cell, an enzyme degrading the sulfur source may vary and a metabolic pathway using the same may also vary according to a structure and a functional group of the sulfur source. For example, when a sulfate is used as the sulfur source, it is known that CysZ transports the sulfate and CysDN, CysH, and CysI are involved until a sulfide is produced (Bolten, Christoph J., Hartwig Schroder, Jeroen Dickschat, and Christoph Wittmann. Towards Methionine Overproduction in *Corynebacterium glutamicum* Methanethiol and Dimethyldisulfide as Reduced Sulfur Sources. *J. Microbiol. Biotechnol.* (2010), 20(8), 1196-1203). However, in the case where thiosulfate is used as a sulfur source in production of sulfur-containing amino acids, factors used to transport and degrade thiosulfate have not been clearly revealed yet.

The sulfur source may be thiosulfate. Specifically, in the present disclosure, the sulfur source may include thiosulfate, such as ammonium thiosulfate or sodium thiosulfate or a mixture of thiosulfate and an organic or inorganic sulfur-containing compound such as sulfite, reduced raw material such as $H_2S$, sulfide, a derivative of sulfide, methylmercaptan, thioglycolite, thiocyanate, and thiourea. Alternatively, the sulfur source may not include any material other than thiosulfate. However, the embodiment is not limited thereto.

The method of producing the sulfur-containing amino acids or derivatives of the sulfur-containing amino acids may include recovering sulfur-containing amino acids or derivatives of the sulfur-containing amino acids from the microorganism or the culture medium.

The recovering step may be performed by collecting desired sulfur-containing amino acids or derivatives of the sulfur-containing amino acids using an appropriate method known in the art according to the culturing method of the present disclosure such as a batch, continuous, or fed-batch method. For example, centrifugation, filtration, treatment with a protein precipitating agent (salting out), extraction, ultrasonic disintegration, ultrafiltration, dialysis, various chromatographic methods such as molecular sieve chromatography (gel permeation), adsorption chromatography, ion-exchange chromatography, and affinity chromatography, high-performance liquid chromatography (HPLC), any combination thereof may be used, without being limited thereto.

The recovering step may further include a purifying process. The purifying process may be performed using an appropriate method known in the art.

Another aspect of the present disclosure provides a composition for producing a sulfur-containing amino acid or a derivative of the sulfur-containing amino acid, wherein the composition includes: a microorganism having enhanced activity of a protein encoded by ssuABC gene compared to intrinsic activity or a culture thereof; and thiosulfate.

The protein encoded by ssuABC gene, microorganism, thiosulfate and sulfur-containing amino acids are as described above.

The culture may be prepared by culturing the microorganism of the present disclosure in a culture medium.

The composition for producing sulfur-containing amino acids or derivatives of the sulfur-containing amino acids according to the present disclosure may further include any component capable of assisting production of the sulfur-containing amino acids or derivatives of the sulfur-containing amino acids, and the component may be appropriately selected from those known in the art.

Another aspect of the present disclosure provides a use of a protein encoded by ssuABC gene as a thiosulfate transporter.

Another aspect of the present disclosure provides a use of a microorganism including genetic modification to increase activity of a protein encoded by ssuABC gene compared to a non-modified microorganism for producing a sulfur-containing amino acid or a derivative of the sulfur-containing amino acid.

The protein encoded by ssuABC gene, microorganism, cultures, thiosulfate, and sulfur-containing amino acid are as described above.

MODE FOR INVENTION

Hereinafter, the present disclosure will be described in more detail with reference to the following examples and experimental examples. However, the following examples and experimental examples are merely presented to exemplify the present disclosure, and the scope of the present disclosure is not limited thereto.

Example 1: Preparation of Recombinant Vector for Deletion of mcbR Gene

First, in order to prepare a strain producing methionine, as a representative sulfur-containing amino acid, *Corynebacterium glutamicum* ATCC 13032 strain was used to prepare a vector for inactivating known mcbR gene encoding a transcriptional regulator protein of methionine and cysteine (*J. Biotechnol.* 103:51-65, 2003).

Specifically, in order to delete the mcbR gene from the chromosome of the *Corynebacterium glutamicum* ATCC 13032 strain, a recombinant plasmid vector was prepared according to the following method.

Based on nucleotide sequences deposited in the U.S. National Institutes of Health (NIH) GenBank, the mcbR gene and flanking sequences (SEQ ID NO: 1) of *Corynebacterium glutamicum* were obtained.

PCR was performed using the chromosomal DNA of *Corynebacterium glutamicum* ATCC 13032 as a template and primers of SEQ ID NOS: 2, 3, 4, and 5. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments of 700 bp were obtained, respectively.

A pDZ vector (U.S. Pat. No. 9,109,242 B2) unable to replicate in *Corynebacterium glutamicum* and the amplified mcbR gene fragments were treated with restriction enzyme SmaI for chromosomal insertion, followed by isothermal assembly cloning. *Escherichia coli* DH5a was transformed with the vector and plated on an LB solid medium containing 25 mg/L kanamycin. Colonies transformed with the vector into which a fragment having deletion of the target gene was inserted by PCR were selected, and then a plasmid was obtained by a plasmid extraction method and named pDZ-ΔmcbR.

Example 2: Preparation and Culture of mcbR Gene-Deleted Strain

The ATCC 13032 strain was transformed with the pDZ-ΔmcbR vector prepared in Example 1 above by electroporation by homologous chromosomal recombination (Van der Rest et al., *Appl Microbiol Biotechnol* 52:541-545, 1999). Subsequently, second recombination was performed in a solid medium containing sucrose. Upon completion of the second recombination, the transformed *Corynebacterium glutamicum* strain having deletion of mcbR gene was identified by performing PCR using SEQ ID NOS: 6 and 7, and the recombinant strain was named CM02-0618.

The CM02-0618 strain was deposited at the Korean Culture Center of Microorganisms under the Budapest Treaty on Jan. 4, 2019, with Accession No. KCCM12425P.

In order to analyze L-methionine producing ability of the prepared CM02-0618 strain, the strain and the parent strain, *Corynebacterium glutamicum* ATCC 13032 strain, were cultured in the following manner.

*Corynebacterium glutamicum* ATCC 13032 and *Corynebacterium glutamicum* CM02-0618 were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows. In the production medium, $(NH_4)_2S_2O_3$, which is one type of thiosulfate, was used as a sulfur source.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4 \cdot 7H_2O$, 100 μg of biotin, 1000 μg of thiamine HCL, 2000 μg of calcium pantothenate, 3000 μg of nicotinamide, 30 g of CaCO₃, and 1 μg of cyanocobalamin (Vitamin B12) (based on 1 L of distilled water).

The strains were cultured according to the above-described culturing method and concentrations of L-methionine contained in the culture broth were analyzed and shown in Table 1 below.

TABLE 1

Confirmation of L-methionine producing ability of wild-type and mcbR gene-deleted strains

| Strain | L-Methionine (g/L) |
|---|---|
| Corynebacterium glutamicum ATCC 13032 (wild-type) | 0.00 |
| CM02-0618 | 0.04 |

As a result, it was confirmed that the L-methionine producing ability of the mcbR gene-deleted strain was enhanced by 0.04 g/L compared to that of the control strain. Also, it was confirmed that methionine was produced even when thiosulfate was used as a single sulfur source.

Example 3: Selection of Thiosulfate Influx Gene by Transcript Analysis

No thiosulfate-specific influx protein of strains of the genus Corynebacterium is known. However, as confirmed in Example 2, the CM02-0618 strain produced methionine when thiosulfate was used as a single sulfur source, and thus an experiment was performed to select a protein involved in influx of thiosulfate.

Specifically, after culturing the CM02-0618 strain prepared in Example 2 by changing only the sulfur source (ammonium sulfate and ammonium thiosulfate), Transcriptome analysis (analysis of RNA level) was performed. The same culturing method as that of Example 2 was used.

TABLE 2

Results of experiment on main gene transcripts of the CM02-0618 strain under the conditions using ammonium sulfate and ammonium thiosulfate

| | AMS (signal) | ATS (signal) | Log2 ratio (ATS/AMS) |
|---|---|---|---|
| SsuC(Ncgl1174) | 2441 | 31316 | 3.68 |
| SsuB(Ncgl1175) | 2136 | 21895 | 3.36 |
| SsuA(Ncgl1176) | 1839 | 21658 | 3.56 |

Based on the results of the experiment, it was confirmed that RNA levels of genes encoding SsuABC (Ncgl1174-76), which is known as a sulfonate transporter, were significantly increased.

Thus, it was confirmed that the SsuABC protein does not react with sulfate but specifically reacts with thiosulfate, and thus it may be assumed that the protein is involved in transport of thiosulfate.

Example 4: Confirmation of Effects of Strain Having Deletion of SsuABC Protein-Encoding Gene A vector was prepared to identify inactivation effects of SsuABC protein selected as a protein specifically reacting with thiosulfate in Example 3.

Example 4-1: Preparation of Vector for Deletion of Gene Encoding SsuABC Protein In order to delete a gene encoding SsuABC protein (hereinafter referred to as ssuABC gene) from the chromosome of Corynebacterium ATCC 13032 strain, a recombinant plasmid vector was prepared according to the following method.

Based on nucleotide sequences deposited in the U.S. National Institutes of Health (NIH) GenBank, the ssuABC gene and flanking sequences (SEQ ID NO: 8) of Corynebacterium glutamicum were obtained.

For the purpose of deleting ssuABC gene, PCR was performed using the chromosomal DNA of Corynebacterium glutamicum ATCC 13032 as a template and primers of SEQ ID NOS: 9, 10, 11, and 12. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments of 700 bp were obtained, respectively.

A pDZ vector unable to replicate in Corynebacterium glutamicum and the amplified ssuABC gene fragments were treated with the restriction enzyme SmaI for chromosomal insertion, followed by isothermal assembly cloning. Escherichia coli DH5a was transformed with the vector and plated on an LB solid medium containing 25 mg/L kanamycin. Colonies transformed with the vector into which a fragment having deletion of the target gene was inserted by PCR were selected, and then a plasmid was obtained by a plasmid extraction method and named pDZ-ΔSsuABC.

Example 4-2: Preparation and Culture of ssuABC Gene-Deleted Strain

13032/ΔmcbR strain was transformed with the pDZ-ΔSsuABC vector prepared in Example 4-1 above by electroporation by homologous chromosomal recombination (Van der Rest et al., Appl Microbiol Biotechnol 52:541-545, 1999). Subsequently, second recombination was performed in a solid medium containing sucrose. Upon completion of the second recombination, the transformed Corynebacterium glutamicum strain having deletion of ssuABC gene was identified by performing PCR using SEQ ID NOS: 13 and 14, and the recombinant strain was named Corynebacterium glutamicum CM02-0618/ΔSsuABC.

Example 4-3: Analysis of Methionine Producing Ability of ssuABC Gene-Deleted Strain In order to analyze L-methionine producing ability of the prepared CM02-0618/ΔSsuABC strain, the strain and the parent strain, Corynebacterium glutamicum ATCC 13032 strain, were cultured in the following manner.

Corynebacterium glutamicum ATCC 13032, Corynebacterium glutamicum CM02-0618 prepared in Example 2, and CM02-0618/ΔSsuABC prepared in Example 4-2 were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>
20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>
50 g of glucose, 12 g of $(NH_4)_2S_2O_3$, 5 g of yeast extract, 1 g of $KH_2PO_4$, 1.2 g of $MgSO_4 \cdot 7H_2O$, 100 μg of biotin, 1000 μg of thiamine HCL, 2000 μg of calcium pantothenate, 3000 μg of nicotinamide, and 30 g of $CaCO_3$ (based on 1 L of distilled water).

The strains were cultured according to the above-described culturing method and concentrations of L-methionine contained in the culture broth were analyzed and shown in Table 3 below.

TABLE 3

Confirmation of L-methionine producing ability of ssuABC gene-deleted strain

| Strain | L-Methionine (g/L) |
|---|---|
| CM02-0618 | 0.12 |
| CM02-0618/ΔSsuABC | 0.03 |

As a result, it was confirmed that the L-methionine producing ability of the ssuABC gene-deleted strain was reduced to 25% compared to that of the control strain. Based thereon, it was confirmed that SsuABC protein is a protein involved in influx of thiosulfate.

Example 5: Preparation and Culture of ssuABC Gene Expression-Enhanced Strain

A vector was prepared to enhance activity of SsuABC protein selected as a protein specifically reacting with thiosulfate in Example 3.

Example 5-1: Preparation of Vector for Enhancement of Expression of ssuABC Gene

In order to additionally inserting ssuABC gene into the chromosome of Corynebacterium ATCC 13032, a plasmid vector was prepared according to the following method.

First, a vector for deleting Ncgl1464 (Transposase) was prepared to insert ssuABC gene.

Based on nucleotide sequences deposited in the U.S. National Institutes of Health (NIH) GenBank, Ncgl1464 gene and flanking sequences (SEQ ID NO: 15) of Corynebacterium glutamicum were obtained. To delete Ncgl1464 gene, PCR was performed using the chromosomal DNA of Corynebacterium glutamicum ATCC 13032 as a template and primers of SEQ ID NOS: 16, 17, 18, and 19. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments were obtained, respectively.

A pDZ vector unable to replicate in Corynebacterium glutamicum and the amplified Ncgl1464 gene fragments were treated with the restriction enzyme SmaI for chromosomal insertion, followed by isothermal assembly cloning. Escherichia coli DH5a was transformed with the vector and plated on an LB solid medium containing 25 mg/L kanamycin. Colonies transformed with the vector into which a fragment having deletion of the target gene was inserted by PCR were selected, and then a plasmid was obtained by a plasmid extraction method and named pDZ-ΔNcgl1464.

Subsequently, for the purpose of obtain ssuABC gene fragments, PCR was performed using the chromosomal DNA of Corynebacterium glutamicum ATCC 13032 as a template and SEQ ID NOS: 20 and 21. In addition, a PgapA promoter was used to enhance expression of the ssuABC gene. To obtain them, PCR was performed using the chromosomal DNA of the Corynebacterium glutamicum ATCC 13032 as a template using primers of SEQ ID NOS: 22 and 23. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, ssuABC gene fragments and gapA promoter fragments were obtained.

A pDZ-ΔNcgl1464 vector unable to replicate in Corynebacterium glutamicum was treated with the restriction enzyme ScaI, followed by isothermal assembly cloning together with the two amplified DNA fragments. Escherichia coli DH5a was transformed with the vector and plated on an LB solid medium containing 25 mg/L kanamycin. Colonies transformed with the vector into which the target gene was inserted by PCR were selected, and then a plasmid was obtained by a plasmid extraction method and named pDZ-ΔNcgl1464-PgapASsuABC.

Example 5-2: Preparation and Culture of ssuABC Gene Expression-Enhanced Strain

CM02-0618 strain was transformed with the pDZ-ΔNcgl1464 and pDZ-ΔNcgl1464-PgapASsuABC vectors prepared in Example 5-1 above by electroporation by homologous chromosomal recombination (Van der Rest et al., Appl Microbiol Biotechnol 52:541-545, 1999). Subsequently, second recombination was performed in a solid medium containing sucrose. Upon completion of the second recombination, the transformed Corynebacterium glutamicum strain having deletion of Ncgl1464 gene and the Corynebacterium glutamicum strain having both deletion of Ncgl1464 gene and insertion of ssuABC gene were identified by performing PCR using primers of SEQ ID NOS: 24 and 25. The strain having deletion of Ncgl1464 gene was named CM02-0618/ΔNcgl1464, and the stain having both deletion of Ncgl1464 gene and insertion of ssuABC gene was named CM02-0735. The CM02-0735 strain was deposited at the Korean Culture Center of Microorganisms under the Budapest Treaty on Mar. 21, 2019, with Accession No. KCCM12466P.

Example 5-3: Analysis of Methionine Producing Ability of ssuABC Gene Expression-Enhanced Strain In order to analyze L-methionine producing ability of the prepared CM02-0618/ΔNcgl1464 and CM02-0735 strains, the strains and the parent strain, CM02-0618 strain, were cultured in the following manner.

Each of the CM02-0618, CM02-0618/ΔNcgl1464, and CM02-0735 strains was inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4·7H_2O$, 100 µg of biotin, 1000 µg of thiamine HCl, 2000 µg of calcium pantothenate, and 2000 µg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4·7H_2O$, 100 µg of biotin, 1000 µg of thiamine HCL, 2000 µg of calcium pantothenate, 3000 µg of nicotinamide, 30 g of $CaCO_3$, and 1 µg of cyanocobalamin (Vitamin B12) (based on 1 L of distilled water).

The strains were cultured according to the above-described culturing method and concentrations of L-methionine contained in the culture broth were analyzed and shown in Table 4 below.

TABLE 4

Confirmation of L-methionine producing ability of ssuABC gene-enhanced strain

| Strain | L-Methionine (g/L) |
|---|---|
| CM02-0618 | 0.04 |
| CM02-0618/ΔNcgl1464 | 0.04 |
| CM02-0735 | 0.07 |

As a result, it was confirmed that the L-methionine producing ability of the ssuABC gene-enhanced strain was increased by 50% or more compared to that of the control strain. Also, it was confirmed that SsuABC protein is involved in influx of thiosulfate as confirmed in Example 4.

Example 6: Comparative Culture between Thiosulfate and Other Sulfonate

SsuABC protein is known as a protein introducing sulfonate (*Appl. Environ. Microbial.* 71 (10:6104-6114, 2005). Sulfonate, having a structure of R—$SO_3$, wherein R is an organic group, is different from thiosulfate, which has a structure of S—$SO_3$.

Thus, effects of thiosulfate on methionine production was identified via a comparative experiment using sulfonate.

*Corynebacterium glutamicum* CM02-0618 and CM02-0735 strains were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4·7H_2O$, 100 µg of biotin, 1000 µg of thiamine HCl, 2000 µg of calcium pantothenate, and 2000 µg of nicotinamide (based on 1 L of distilled water).

<Production Medium (pH 8.0)>

50 g of glucose, 12 g of $(NH_4)_2S_2O_3$, methane sulfonate, or ethane sulfonate (depending on the sulfur source), 5 g of yeast extract, 1 g of $KH_2PO_4$, 1.2 g of $MgSO_4·7H_2O$, 100 µg of biotin, 1000 µg of thiamine HCL, 2000 µg of calcium pantothenate, 3000 µg of nicotinamide, 30 g of $CaCO_3$, and 1 µg of cyanocobalamin (Vitamin B12) (based on 1 L of distilled water).

The strains were cultured according to the above-described culturing method and concentrations of L-methionine contained in the culture broth were analyzed and shown in Table 5 below.

TABLE 5

Comparison of methionine producing ability between thiosulfate and various sulfonates as sulfur sources

| Strain | Sulfur source | L-Methionine (g/L) |
|---|---|---|
| CM02-0618 | thiosulfate | 0.04 |
|  | methane sulfonate | 0.01 |
|  | ethane sulfonate | 0.01 |
| CM02-0735 | thiosulfate | 0.07 |
|  | methane sulfonate | 0.01 |
|  | ethane sulfonate | 0.02 |

As a result, in the case where thiosulfate was used as the sulfur source in each strain, the production of methionine increased by up to 700% compared to the case of using sulfonate as the sulfur source. Based thereon, it was confirmed the production of methionine was the highest when thiosulfate was used as the sulfur source, and it was also confirmed that enhancement of the activity of SsuABC protein is involved in such an increase in production of methionine.

Example 7: Preparation of Methionine-Producing Strain Having Enhanced metH and cysI Genes without Deleting mcbR Gene Example 7-1: Preparation of Recombinant Vector for Enhancing Both metH and cysI Genes In order to identify whether production of a sulfur-containing amino acid is increased by enhancing the activity of the SsuABC protein of the present disclosure and using thiosulfate as a sulfur source, the above-described experiment was applied to another methionine-producing strain. First, a vector for enhancing both metH gene (Ncgl1450) encoding a methionine synthase and cysI gene (Ncgl2718) encoding a sulfite reductase in the ATCC 13032 strain was prepared.

Specifically, a recombinant plasmid vector was prepared to additionally insert metH and cysI genes into the chromosome of *Corynebacterium glutamicum* ATCC 13032 according to the following method. Based on nucleotide sequences deposited in the U.S. National Institutes of Health (NIH) GenBank, the metHgene and flanking sequences (SEQ ID NO: 26) and the cysI gene and flanking sequences (SEQ ID NO: 27) of *Corynebacterium glutamicum* were obtained.

First, a vector for deleting Ncgl1201 (Transposase) was prepared to insert these genes. Based on nucleotide sequences deposited in the U.S. National Institutes of Health (NIH) GenBank, Ncgl1021 gene and flanking sequences (SEQ ID NO: 28) of *Corynebacterium glutamicum* were obtained. To delete Ncgl1021 gene, PCR was performed using the chromosomal DNA of *Corynebacterium glutamicum* ATCC 13032 as a template and primers of SEQ ID NOS: 29, 30, 31, and 32. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments were obtained. A pDZ vector unable to replicate in *Corynebacterium glutamicum* and the amplified Ncgl1021 gene fragments were treated with restriction enzyme XbaI for chromosomal insertion, followed by isothermal assembly cloning. *Escherichia coli* DH5a was transformed with the vector and plated on an LB solid medium containing 25 mg/L kanamycin. Colonies transformed with the vector into which a fragment having deletion of the target gene was inserted by PCR were selected, and then a plasmid was obtained by a plasmid extraction method and named pDZ-ΔNcgl1021.

Subsequently, for the purpose of obtaining metH and cysI genes, PCR was performed using the chromosomal DNA of *Corynebacterium glutamicum* ATCC 13032 as a template and primers of SEQ ID NOS: 33, 34, 35, and 36. In addition, a Pcj7 promoter was used to enhance expression of the metH gene and a Pspl1 promoter was used to enhance expression of the cysI gene. To obtain them, PCR was performed using the chromosomal DNA of the *Corynebacterium ammoniagenes* ATCC 6872 as a template and using primers of SEQ ID NOS: 37 and 38 for the Pcj7 promotor and PCR was performed using DNA of known spl1-GFP vector (U.S. Ser. No. 10/584,338 B2) as a template and using primers of SEQ ID NOS: 39 and 40 for the Pspl1 promotor. PCR was performed under the following conditions: denaturation at 95° C. for 5 minutes; 30 cycles of denaturation at 95° C. for 30 seconds, annealing at 53° C. for 30 seconds, and polymerization at 72° C. for 30 seconds; and polymerization at 72° C. for 7 minutes. As a result, DNA fragments of metH and cysI genes, Pcj7 promoter (U.S. Pat. No. 7,662,943 B2), and Pspl1 promoter (U.S. Ser. No. 10/584,338 B2) were obtained.

A pDZ-ΔNcgl1021 vector unable to replicate in *Corynebacterium glutamicum* was treated with the restriction enzyme ScaI and the amplified four DNA fragments were treated with the restriction enzyme ScaI, followed by isothermal assembly cloning. *Escherichia coli* DH5a was transformed with the vector and plated on an LB solid medium containing 25 mg/L kanamycin. Colonies transformed with the vector into which the target gene was inserted by PCR were selected, and then a plasmid was obtained by a plasmid extraction method and named pDZ-ΔNcgl1021-Pcj7metH-Pspl1cysI.

Example 7-2: Development of L-Methionine-Producing Strain and Identification of L-Methionine Production Using the Same The ATCC 13032 strain was transformed with the pDZ-ΔNcgl1021 and pDZ-ΔNcgl1021-Pcj7metH-Pspl1 cysI vectors prepared in Example 7-1 above by electroporation by homologous chromosomal recombination (Van der Rest et al., *Appl Microbiol Biotechnol* 52:541-545, 1999). Subsequently, second recombination was performed in a solid medium containing sucrose. Upon completion of the second recombination, insertion of the Pcj7-metH-Pspl1 cysI gene into the transformed *Corynebacterium glutamicum* strain was identified using SEQ ID NOS: and 41 and 42. The recombinant strains were named *Corynebacterium glutamicum* 13032/ΔNcgl1021 (strain transformed with pDZ-ΔNcgl1021) and CM02-0753 (transformed with pDZ-ΔNcgl1021-Pcj7metH-Pspl1cysIn).

To analyze L-methionine producing ability of the prepared 13032/ΔNcgl1021 and CM02-0753 strains, the strains and the parent strain, *Corynebacterium glutamicum* ATCC 13032 strain, were cultured in the following manner.

*Corynebacterium glutamicum* ATCC 13032 and strains of the present disclosure, i.e., *Corynebacterium glutamicum* 13032/ΔNcgl1021 and CM02-0753 were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4·7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4·7H_2O$, 100 μg of biotin, 1000 μg of thiamine HCL, 2000 μg of calcium pantothenate, 3000 μg of nicotinamide, 30 g of $CaCO_3$, and 1 μg of cyanocobalamin (Vitamin B12) (based on 1 L of distilled water).

The strains were cultured according to the above-described culturing method and concentrations of L-methionine contained in the culture broth were analyzed and shown in Table 6 below.

TABLE 6

Confirmation of L-methionine producing ability of mcbR gene-containing strain

| Strain | L-Methionine (g/L) |
| --- | --- |
| *Corynebacterium glutamicum* ATCC 13032 (wild-type) | 0 |
| 13032/ΔNcgl1021 | 0 |
| CM02-0753 | 0.03 |

As a result, it was confirmed that the L-methionine producing ability of the strain in which the mcbR gene was present and the metH and cysI genes were overexpressed was enhanced compared to that of the controls train. Based thereon, it was confirmed that the strain in which the metH and cysI genes were overexpressed without deleting the mcbR gene had the methionine producing ability, and the strain was used in the following experiment.

Example 8: Development of L-Methionine-Producing Strain Having Enhanced SsuABC Activity and Including mcbR and Identification of L-Methionine Producing Ability A strain having enhanced expression of SsuABC protein was prepared using the methionine-producing strain prepared in Example 7, and then the L-methionine producing ability thereof was identified.

Example 8-1: Preparation of Strain Having Enhanced SsuABC Activity

Specifically, the CM02-0753 strain of Example 7 was transformed with the pDZ-ΔNcgl464-PgapASsuABC vector prepared in Example 5 by electroporation by homologous chromosomal recombination (Van der Rest et al., *Appl Microbiol Biotechnol* 52:541-545, 1999). Subsequently, second recombination was performed in a solid medium containing sucrose.

Upon completion of the second recombination, insertion of PgapA-SsuABC gene into the Ncgl1464 site of the transformed *Corynebacterium glutamicum* was identified using SEQ ID NOS: 24 and 25. The prepared recombinant strain was named *Corynebacterium glutamicum* CM02-0755.

The CM02-0755 was deposited at the Korean Culture Center of Microorganisms under the Budapest Treaty on Mar. 21, 2019, with Accession No. KCCM12467P.

Example 8-2: Identification of Methionine Producing Ability of Prepared Strain

In order to analyze L-methionine producing ability of the prepared CM02-0753 strain of Example 7 and CM02-0755 strain prepared in Example 8-1, the strains were cultured in the following manner.

*Corynebacterium glutamicum* CM02-0753 and CM02-0755 strains were inoculated onto a 250 mL corner-baffle flask containing 25 mL of a seed medium and cultured while shaking at 30° C. for 20 hours at 200 rpm. Then, 1 mL of a culture broth thereof was inoculated onto a 250 mL corner-baffle flask containing 24 mL of a production medium and cultured while shaking at 30° C. for 48 hours at 200 rpm. The compositions of the seed medium and the production medium are as follows.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine HCl, 2000 μg of calcium pantothenate, and 2000 μg of nicotinamide (based on 1 L of distilled water).

<Production Medium (pH 8.0)>

50 g of glucose, 12 g of $(NH_4)_2S_2O_3$, 5 g of yeast extract, 1 g of $KH_2PO_4$, 1.2 g of $MgSO_4 \cdot 7H_2O$, 100 μg of biotin, 1000 μg of thiamine HCL, 2000 μg of calcium pantothenate, 3000 μg of nicotinamide, 30 g of $CaCO_3$, and 1 μg of cyanocobalamin (Vitamin B12) (based on 1 L of distilled water).

The strains were cultured according to the above-described culturing method and concentrations of L-methionine contained in the culture broth were analyzed and shown in Table 7 below.

TABLE 7

Confirmation of L-methionine producing ability of mcbR gene-containing strain when ssuABC gene is overexpressed

| Strain | L-Methionine (g/L) |
|---|---|
| CM02-0753 | 0.03 |
| CM02-0755 | 0.05 |

As a result, it was confirmed that the L-methionine producing ability was enhanced by increasing activity of SsuABC protein in the presence of mcbR and using thiosulfate as the sulfur source.

These results indicate that sulfur-containing amino acids or derivatives of the sulfur-containing amino acids may be produced using thiosulfate as a sulfur source by enhancing the activity of SsuABC protein that is newly confirmed in the present disclosure as a thiosulfate influx protein.

The above description of the present disclosure is provided for the purpose of illustration, and it would be understood by those skilled in the art that various changes and modifications may be made without changing the technical conception and essential features of the present disclosure. Thus, it is clear that the above-described embodiments are illustrative in all aspects and do not limit the present disclosure. Therefore, the scope of the disclosure is defined not by the detailed description, but by the claims and their equivalents, and all variations within the scope of the claims and their equivalents are to be construed as being included in the disclosure.

What is claimed is:

1. A method of producing a sulfur-containing amino acid or a derivative of the sulfur-containing amino acid, the method comprising culturing a genetically modified microorganism in a culture medium including thiosulfate,
    wherein the microorganism includes genetic modification to increase an expression level of a protein encoded by ssuABC gene compared to a non-modified microorganism,
    wherein the protein encoded by ssuABC gene is a complex of SsuA, SsuB, and SsuC proteins, and wherein the sulfur-containing amino acid or the derivative of the sulfur-containing amino acid is selected from the group consisting of methionine, cysteine, cystine, lanthionine, homocysteine, homocystine, homolanthionine, and taurine, and
    wherein the microorganism has an increase in an expression level of at least one protein selected from the group consisting of SsuA, SsuB, and SsuC proteins compared to a non-modified microorganism.

2. The method of claim 1, wherein the protein encoded by ssuABC gene has thiosulfate transporter activity.

3. The method of claim 1, wherein the microorganism has an increase in an expression level of SsuA, SsuB, and SsuC proteins compared to a non-modified microorganism.

4. The method of claim 1, wherein the SsuA protein includes an amino acid sequence having at least 80% of homology with an amino acid sequence of SEQ ID NO: 43.

5. The method of claim 1, wherein the SsuB protein includes an amino acid sequence having at least 80% of homology with an amino acid sequence of SEQ ID NO: 44.

6. The method of claim 1, wherein the SsuC protein includes an amino acid sequence having at least 80% of homology with an amino acid sequence of SEQ ID NO: 45.

7. The method of claim 1, wherein the microorganism is a microorganism belonging to the genus *Corynebacterium* sp. or the genus *Escherichia* sp.

8. The method of claim 1, further comprising recovering the sulfur-containing amino acid or the derivative of the sulfur-containing amino acid from the microorganism or the culture medium.

9. The method of claim 1, wherein genetic modification to increase the expression level of the protein is achieved by i) increasing a copy number of a polynucleotide encoding the protein in a cell, ii) replacing an expression regulatory region of a polynucleotide encoding the protein with a sequence with stronger activity, iii) modifying an initiation codon or 5'-UTR of a polynucleotide encoding the protein, iv) modifying a nucleotide sequence on a chromosome to enhance the activity of the protein, v) introducing a foreign polynucleotide expressing the activity of the protein or a codon optimized variant polynucleotide of the polynucleotide encoding the protein, or vi) a combination thereof.

10. A microorganism producing a sulfur-containing amino acid or a derivative of the sulfur-containing amino acid and including genetic modification to increase an expression level of a protein encoded by ssuABC gene compared to a non-modified microorganism, wherein the protein encoded by ssuABC gene is a complex of SsuA, SsuB, and SsuC proteins, and wherein the sulfur-containing amino acid or the derivative of the sulfur-containing amino acid is selected from the group consisting of methionine, cysteine, cystine, lanthionine, homocysteine, homocystine, homolanthionine, and taurine, and wherein the microorganism produces the sulfur-containing amino acid or the derivative of the sulfur-containing amino acid using thiosulfate as a sulfur source.

11. The microorganism of claim 10, wherein genetic modification to increase the expression level of the protein is achieved by i) increasing a copy number of a polynucleotide encoding the protein in a cell, ii) replacing an expression regulatory region of a polynucleotide encoding the protein with a sequence with stronger activity, iii) modifying an initiation codon or 5'-UTR of a polynucleotide encoding the protein, iv) modifying a nucleotide sequence on a chromosome to enhance the activity of the protein, v) introducing a foreign polynucleotide expressing the activity of the protein or a codon optimized variant polynucleotide of the polynucleotide encoding the protein, or vi) a combination thereof.

12. A composition for producing a sulfur-containing amino acid or a derivative of the sulfur-containing amino acid,
wherein the composition comprises: a microorganism including genetic modification to increase an expression level of a protein encoded by ssuABC gene compared to a non-modified microorganism, or a culture thereof; and thiosulfate;
wherein the protein encoded by ssuABC gene is a complex of SsuA, SsuB, and SsuC proteins, and wherein the sulfur-containing amino acid or the derivative of the sulfur-containing amino acid is selected from the group consisting of methionine, cysteine, cystine, lanthionine, homocysteine, homocystine, homolanthionine, and taurine.

* * * * *

SEQUENCE LISTING

```
<160> NUMBER OF SEQ ID NOS: 45

<210> SEQ ID NO 1
<211> LENGTH: 2642
<212> TYPE: DNA
<213> ORGANISM: Corynebacterium glutamicum

<400> SEQUENCE: 1
ctcccgcgca ctgctgcaat ccgcaccgtg cccaatgatg gtggttcgcc cacctgagaa      60
gattaagaag tagtttcttt taagtttcga tgccccggtt tcctgatttt gtgcagggag     120
gccggggcat tggtgtttgc gggttagttc gggccattcg aaagggagaa accaagggca     180
gccagacaga cgtgccaaga atctggattt ccgccaggtt ttggcacgcc cgtctggttt     240
aggcaatgag ataccgaaca cacgtgccaa aagttcggct ttttcgccga tcttgtcacg     300
cctgcctggt ttgtcttgta aagagtgatt tcatggccga gactcctaaa agtttgacct     360
cacaggattg cttctaaggg cctctccaat ctccactgag gtacttaatc cttccgggga     420
attcgggcgc ttaaatcgag aaattaggcc atcaccttttt aataacaata caatgaataa     480
ttggaatagg tcgacacctt tggagcggag ccggttaaaa ttggcagcat tcaccgaaag     540
aaaaggagaa ccacatgctt gccctaggtt ggattacatg gatcattatt ggtggtctag     600
ctggttggat tgcctccaag attaaaggca ctgatgctca gcaaggaatt ttgctgaaca     660
```

-continued

```
tagtcgtcgg tattatcggt ggtttgttag gcggctggct gcttggaatc ttcggagtgg      720
atgttgccgg tggcggcttg atcttcagct tcatcacatg tctgattggt gctgtcattt      780
tgctgacgat cgtgcagttc ttcactcgga agaagtaatc tgctttaaat ccgtagggcc      840
tgttgatatt tcgatatcaa caggccttt  ggtcatttg gggtggaaaa agcgctagac       900
ttgcctgtgg attaaaacta tacgaaccgg tttgtctata ttggtgttag acagttcgtc      960
gtatcttgaa acagaccaac ccgaaaggac gtggccgaac gtggctgcta gcgcttcagg     1020
caagagtaaa acaagtgccg gggcaaaccg tcgtcgcaat cgaccaagcc cccgacagcg     1080
tctcctcgat agcgcaacca accttttcac cacagaaggt attcgcgtca tcggtattga     1140
tcgtatcctc cgtgaagctg acgtggcgaa ggcgagcctc tattcccttt tcggatcgaa     1200
ggacgccttg gttattgcat acctggagaa cctcgatcag ctgtggcgtg aagcgtggcg     1260
tgagcgcacc gtcggtatga aggatccgga agataaaatc atcgcgttct tgatcagtg      1320 cattgaggaa gaaccagaaa aagatttccg cggctcgcac tttcagaatg cggctagtga     1380
gtaccctcgc cccgaaactg atagcgaaaa gggcattgtt gcagcagtgt tagagcaccg     1440
cgagtggtgt cataagactc tgactgattt gctcactgag aagaacggct acccaggcac     1500
cacccaggcg aatcagctgt tggtgttcct tgatggtgga cttgctggat ctcgattggt     1560
ccacaacatc agtcctcttg agacggctcg cgatttggct cggcagttgt tgtcggctcc     1620
acctgcggac tactcaattt agtttcttca ttttccgaag gggtatcttc gttggggag      1680 gcgtcgataa gccccttctt tttagcttta acctcagcgc gacgctgctt taagcgctgc     1740
atggcggcgc ggttcatttc acgttgcgtt tcgcgcctct tgttcgcgat ttctttgcgg     1800
gcctgttttg cttcgttgat ttcggcagta cgggttttgg tgagttccac gtttgttgcg     1860
tgaagcgttg aggcgttcca tggggtgaga atcatcaggg cgcggttttt gcgtcgtgtc     1920
cacaggaaga tgcgcttttc ttttgtttt  gcgcggtaga tgtcgcgctg ctctaggtgg     1980
tgcactttga aatcgtcggt aagtgggtat ttgcgttcca aaatgaccat catgatgatt     2040
gtttggagga gcgtccacag gttgttgctg acccaataga gtgcgattgc tgtggggaat     2100
ggtcctgtga ggccaaggga cagtgggaag atcggcgcga ggatcgacat cacgatcatg     2160
aacttcagca tgccgttaga gaatccggat gcgtaatcgt tggtttggaa gctgcggtac     2220
atggacatcg ccatgttgat tgcggtgagg attgcggctg tgatgaacag tggcaaaacg     2280
aaactaagaa cttccgcctg cgtggtgctc aaatattta  gctgctcagt gggcatcgaa     2340
acataagcgc gcagaggcac attgctcacg cgaccagcgg ggaaagattc cacttcctca     2400
ggagttagga agccgatcga ctggaagacg ggattttcca aaccaccttc agggcgagcc     2460
atgcggagaa gtgcccagta aagaccaagg acaatcggta tctggatcag cccaggcaca     2520
caacctgcca gcgggttaat gccgtattcc ttattcaaat cattctggcg cttctgcaac     2580
tcccgaatgg acgcttcatc gtactttccc ttgtattctt cccggagcgc agcgcggtga     2640
gg                                                                   2642
```

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2

```
tcgagctcgg taccoctgcc tggtttgtct tgta                              34

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
cggaaaatga agaaagttcg gccacgtcct ttcgg                             35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
aggacgtggc cgaactttct tcattttccg aaggg                             35

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
ctctagagga tccccgtttc gatgcccact gagca                             35

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
aatctggatt tccgccaggt                                              20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cttcctaact cctgaggaag                                              20

<210> SEQ ID NO 8
<211> LENGTH: 4528
<212> TYPE: DNA
<213> ORGANISM: Corynebacterium glutamicum

<400> SEQUENCE: 8
atgcgtggat tactgacgct tctttgattg aggcgacaaa acgcttgaag ttcctcgttg    60
cgcttcgccc tgggcagatt ggacctacgc tgtctgctca aatggcttct actttccagc   120
gtctgtctgg caaccgtttg ctgatcaatg tggtcaccgg tggggaagat gcggagcagc   180
gtgcgttttg tgatttcttg aacaaggagg agcgctacgc ccgtaccgga gaattcttgg   240
atatcgtgag ccgcttgtgg cgaggcgaaa ccgtcacgca ccacggtgaa cacctgcagg   300
```

```
tggagcaagc tagccttgcg catccgccag agattattcc ggagattctt tttggtggat    360
cgtcgccagc tgcaggtgag gtggctgcac gttatgcgga cacctatctc acgtggggtg    420
aaactcccga tcaggtggcg cagaaaatca actggatcaa cgagctagca gcacagcgcg    480
gccgggaact cgccatgga atccgcttcc atgtgatcac ccgcgatacg tctgaagaag     540
catgggtggt ggcagagaag ttgattagcg gggtcactcc agaacaggtc gctaaggctc    600
aagccgggtt tgcaacgtct aagtcggagg ggcagcgccg gatggctgag ctgcacagca    660
agggtcgtgc ctttactagt ggctcaactg ctcgtgatct ggaggtgtat cccaatgtgt    720
gggcaggcgt cggtttgctt cgcggaggtg caggaacagc ccttgtgggc tcgcatgaag    780
aggtcgccga tcgcatcgaa gaatacgcag cactcggctt ggatcagttt gtactgtcgg    840
gttatccaaa cttggaggag ccttccact tcggtgaggg tgtgattccg gagctgctgc    900
gccgcggtgt ggatatcaaa atcaagaat cacgagtttt ggaacctgtt gggtaaacgg     960
gaagaacgag acgtcgataa gcaaatttct taaggaacct gacatgacta caaccttgac   1020
tcgcccaaa atcgcgctgc ccgcgcgcat ctattcaccg cttgcggtgc ttgttttctg    1080
gcagctcggc tcgagcctgg gcgccatccc ggagcggatt ctgccggcac caaccacgat   1140
cttggccgcc agctgggagg tcgccacaaa tggcacgctt ctcgacgccc tcctcgtctc   1200
aagccaacgc gtccttctag gcttcgccct cggtgctgtc ctaggcattt ccctaggtgt   1260
attgacaggc atgtccagat tgcagacac cgccgttgat ccgctcattc aagctgcccg    1320
cgcgctgcct cacctgggtc ttgtgccgct gtttatcatc tggttcggta tcggtgagct   1380
gccgaaagta ctgattatta gcctcggcgt gctgtatccg ctgtacctca acaccgccag   1440
cgggttcagg caaattgatc caaagcttct ggaagccggc cacgtgatgg gcttcggatt   1500
tttccagagg ttgcggacca tcatcattcc ttctgccgcg ccgcaacttt ttgtcggcct   1560
gcgccaagca agtgcggccg cctggctctc actgatcgtg gcggaacagg tcaacgcccg   1620
cgaaggactc ggcttcctca tcaacaatgc gcgcgatttt taccgcaccg acctcgttat   1680
tttcggcctc attgtctacg ccagcctcgg tctgctgtct gaagcgctga tcagagcttg   1740
ggaacgtcac accttccgct accgaaacgc ataagaaagt tgctcgccat gactgccaca   1800
ttgtcactca aaccccgcagc cactgtccgt ggattgcgca aatcatacgg aactaaagaa   1860
gtcctccaag gaatcgacct caccatcaac tgcggcgaag taaccgcgct gatcggacgc   1920
tcaggttcag gaaaatccac catcctgcgc gtgttggcgg gcctatctaa agagcattcc   1980
ggctctgtag aaatttccgg aaacccggcc gttgccttcc aagagcctcg cctgttgccg   2040
tggaaaacgg tgctcgataa tgtgacccttt ggcctcaacc gcactgatat ttcctggtca   2100
gaagcacaag aacgcgcctc ggcactgctt gcagaagtca aacttcccga ctccgacgcc   2160
gcctggcccc tcacgctctc cggcggccaa gcccagcgcg tctcccttgc gcgagcgctc   2220
atctccgagc cagagctttt gcttctcgac gaacccttcg gcgccctcga tgctctgaca   2280
agactgacag cccaagacct gctgctcaaa accgtgaaca cccgaaactt gggagttctg   2340
ctggtcaccc atgatgtttc cgaggccatc gccctggccg accacgtcct tcttcttgac   2400
gacggcgcca tcacacacag tttgactgta gatatccccg cgatcgccg cacccacccc    2460
tcctttgcct cctacaccgc tcaactcctt gagtggctcg aaatcaccac acctgcctag   2520
aaagaaatca tgaaatttaa gaaatcgccc tcgttctcg ccttcggtct aggccttgca    2580
tcctgctcat cagcttctgg cgatcccgcc accaacgccg atggatccat cgatctgagc   2640
```

| | | | | | |
|---|---|---|---|---|---|
| aaagtaaccc | ttaacatcgg | tgatcaaatc | gccggaacag | aacaagtgct | ccaagcttca | 2700 |
| ggggagctag | atgatgtccc | ttataaaatc | gaatggtcat | catttacctc | tggaccaccc | 2760 |
| caaatcgaag | cattaaacgc | aggtcaaatt | gatttcgcga | tcaccggaaa | caccccaccg | 2820 |
| atcatcggcg | gccccaccaa | caccaaagtg | gtctccgcct | acaacaacga | tgctttaggt | 2880 |
| gatgtcatct | tggtcgcccc | ggattcttca | ataacctcgg | tggctgacct | tgctggaaag | 2940 |
| aaagtggctg | tcgcccgcgg | atccagcgcc | cacggacacc | tcatccaaca | actagaaaaa | 3000 |
| gcaggcgtga | gcgttgacga | cgtagaaatc | aacctcctcc | aaccctccga | cgccaaagcc | 3060 |
| gctttccaaa | acggccaggt | agatgcgtgg | gcagtgtggg | atccctacag | ctcacaggcg | 3120 |
| gaactggaag | gagctcaagt | tttggtcagg | ggagcgggac | tggtcagtgg | gcatggattt | 3180 |
| ggtgtcgcaa | gtgatgaagc | gctcgatgac | cccgcaaagg | aagccgcctt | ggcagatttc | 3240 |
| ctcgatcgcg | tggccgactc | ttatgaatgg | gctgaagaca | caccgatga | atgggcgacg | 3300 |
| attttcagcc | aagaatccgg | ctttgatccg | gaggcctctc | aactgaacac | ccgcagcctg | 3360 |
| cgccatcagg | tgccgctcga | cgagtccgtc | aacacctatc | agaacgcgct | tatcgacgct | 3420 |
| ttcgtctccg | cgggtctcgt | tgaggacttt | aatttcgagg | acaccgtaga | caccgatttt | 3480 |
| gagggctaag | tatgtctgag | tatggcaaag | gggcgttgag | gtgctcagac | ggccatacaa | 3540 |
| agcatcgtag | tttgtgcata | tgagggctgc | tttttgccgc | tgtgagttgg | ctgttcagga | 3600 |
| atccgtcctc | gggttgggga | gagggctga | aaccgaacga | atattcgcat | aaatctttcg | 3660 |
| aattggcgcg | aatattcgat | cccgctggcc | tccgaactag | ccattttggt | agaaaatttg | 3720 |
| catccttgag | ccggtattgg | cccaaggatg | catttcctg | tgtcctactt | ctgcagtgag | 3780 |
| tagaactgag | cactcatcgc | tgggacatgc | agtgagagtg | agtaggcgaa | attatcgcgt | 3840 |
| ggtgtcgctc | ctgcttgaac | ggaagtagcg | atatcgtttt | ctgcaccgag | gaattcagca | 3900 |
| tcatcagtgt | tgagaacgag | cttccattcg | ccaccgctg | caacaccgag | ctggtactca | 3960 |
| ggctgggagg | ttccagacag | gttgaataca | cacagcatct | gggagccgtc | gctgccgaaa | 4020 |
| cgagtgaacg | ccaaaatgtt | gttggtggcg | tcgtcgccct | tattccatgt | gaagccttct | 4080 |
| ccggtgaaat | cctgagtgtg | cagcgcaggg | gagtctgagt | agacaccgtt | gagggagcgg | 4140 |
| gtcagagtgc | ggatggcttc | gtggtactcg | ccttgccagc | cgtcgacaat | atcccatggc | 4200 |
| agtccctggc | cttcagccca | ctcttcacgc | tgaccaaact | cctgacccat | gaaaagcagc | 4260 |
| ttcttgcctg | ggtgtgacca | catgtacgca | aggaaggtgc | gaagaccagc | ggccttgttc | 4320 |
| cacgtatcgc | caggcatacg | gtcccacagg | gaacccttgc | cgtggacgac | ttcatcgtga | 4380 |
| gagatcggaa | gtacaaaacg | ctcagagaat | gcgtacacca | aggagaaagt | gagctcactg | 4440 |
| tggtggaatg | cgcggtgcac | agggttttg | gagaagtact | ctaaggtgtc | gtgcatccag | 4500 |
| cccatgttcc | acttgaggga | gaatccca | | | | 4528 |

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
tcgagctcgg tacccagcaa gctagccttg cgcat        35

<210> SEQ ID NO 10
<211> LENGTH: 35

```
<212> TYPE: DNA
<213> ORGANISM: Artificial Sequence
<220> FEATURE:
<223> OTHER INFORMATION: primer

<400> SEQUENCE: 10
cagacataca gtactgtcag gttccttaag aaatt                              35

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
gaacctgaca gtactgtatg tctgagtatg gcaaa                              35

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
ctctagagga tccccttgtc gacggctggc aaggc                              35

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ccaggtgttt ggggtgcagg                                               20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
agtttggtca gcgtgaagag                                               20

<210> SEQ ID NO 15
<211> LENGTH: 3161
<212> TYPE: DNA
<213> ORGANISM: Corynebacterium glutamicum

<400> SEQUENCE: 15
agacgattct ggaaggccac tttcttttga tcctggcggc gattttcgg tgcttggtag     60 cggaatgtca atcgagacca agcgtccccc ggcgggtcga ttttttggtc tcgaatgaca   120
gtttcgctct ctggaaactc tcagtgtcag gtcagtggtg aaccaccatc cttagcaagg   180
agttcatcat gtccatcccc ttctcagtcc ttcaggacta cctggatctg atcagtcccg   240
aagccttacc ccagatccca cagccccgg ccctgcccc cacagcaccc cagctaccac     300
cggcgccgga cccacacagc atcgagtggc cgatcttccc accagatcga atctccgcca   360
acgggcgacg ctactacgag ccacaaacac gactcgagtt catgcggatc tacaccaccc   420
```

```
tgccgcacgg ctaccgccag cccttcctta aagccaacaa catcggccac tgcaccgttc    480
gaacctggct agcagcaata agcaccttca gccgacttcc ccatgctttt gatgatgccc    540
accgcttcgg gatcgaacgc accaccccag tcgacgatgt caccacacta acggctgatg    600
acaaacgtga cctggtcata ggatacttag ctcaaccaca cggtcagggc cagcaattcc    660
tcacgtttta ccaactccgt aagcacacca tcatggcctg gtgcgccgct atgaccgacg    720
gggacttaga cgctgatatc tcaccccgcc agatcgggtt gatgaccacc cgaaccgtgg    780
tcgaaatcgt tcgactacgc cacatgattg cccaacaact agaaagagcc acgatcatgg    840
aaaacgagta cctcaaagaa atcgcagcgc tgaagaaaga actcgcgcac tacaagcaaa    900
aagaccatca gaatcaaatg gtgatcgata tcttgggaaa agctattggg accaggccca    960
atcctggcga gggcttagac gaggaggacg ccacctaaac gtggatgagc aacgcgcctt   1020
tgatcaagga ctcaaggaag aaaacacctt gatcacagat ctcaccacct gtgccaggct   1080
gagccataac aaggcattac ggctgatcaa gctgtcgaaa tcaacggcgt attaccgcaa   1140
caagccgcgt ccccgtcctg caccgaaacc tgtcctgcag gccgtgccag caccaacagc   1200
acctggtgtg gaacccacac cagagccttg gcagggaag gagccagcag tgtcgtcggt    1260
gcgtcaagcg ttggcagaac acgaacgcca gttcattgtt gatgcgatca ccgcgtaccc   1320
acaactgagc gttagtgggg tgtttaacat gttgtttaac aaaggcatct accgcgcatc   1380
actacgtaca tggtggcgtg ttgccaagca gcacaagttg ttacacaaag accgagtcag   1440
tgccctgtcc ccggggaaac gatcaccaac gccacgggtt aagccgaggt tggaagcaac   1500
acagcctggt caggtggtgt gttgggatgt gacgttcttg ccgtcgctgg tacgtggtaa   1560
gacctatgcg ttgcatctgg cgattgattt gttttcccgc aagattgttg gggcgaaggt   1620
cgcgccgacg gaaaatacct ccaccgcggt ggagttgtta acgcaggtgt tagcggataa   1680
tccgggtgtg gtgacggtgc attcggataa tgggtcggcg atgacatcga cgagggtgcg   1740
gcggttgtta gcggatcatg gtgtggcgtt gtcgttgatt cggccgcggg tgagtgatga   1800
taatgcgttt gtggagtcgg tgtttcatac gttgaagtat cggccgtttt atccgaaggt   1860
gtttgcatcg atggatcagg cccgggtgtg ggtggaggag tttgtggtgt attacaacac   1920
ggttcatccg cattctggtg tggctgggca tactccgcag tcggtgtttg atggtagttg   1980
gagggcggct cataggttgc gtgtgcaggc gttggatgcc cattaccggc agttcccgca   2040
gcggtatgtg gggcggccgg tggttcagga agttgctggt gtggtgcgtc ttaatggtgc   2100
gcgtgatgat gggtctgtac aggagagggt tggtggtgta cgtcgctgt taagtgcttg    2160 agttagcatg tgttcttatc gccccctgg ttcacaaacc cctggcagcg agcggaaaag    2220
tgcattttta ggccaagggc cctcggatct tcgagcgctt tggtctcttt tgcacgtctg   2280
accgaaccag atcacctaga aacgccaaag gccccgcaag tatcaaacct gcgggcctt    2340 tgaggtacct gtttcctatt tgttgacttg aggaagctgc gcacggcgga taaccaaacc   2400
gcacagcaag gcagccactc cccacgcggt gagccagaac tgctccacga cataaacctg   2460
aatagttgga agcaaacgac ttacgatcac cagggctaca gcgatgctca agaaatgat    2520 ctgtgtcttt gagcttggct cgtacttgct ggtggtagcg aatgcgccga gaatgatcga   2580
ggcaacgagg atcagaagga atcctggagt gatcacaaat gggctcagca tgccggcggt   2640
aaacagctca attgctgcaa acaccaacaa aaccagacct aaggctacga aagctccacc   2700
gatgcggatt gctgccggaa ctttacgcca gctggcacgg ccttcgaggc tggtgagctt   2760
ttttaatgat cttcccgatg ctgaactcat aatgtgacat accctactag ttctcgtacc   2820
```

```
atccccacac aattgacctg ccaagagtgt ggaaatacag gttgaagcct agaacagtgg    2880
gggtagcgtc gggggcgatg tcgagttttt ccacatcaag tgcatgaact gcgaagaggt    2940
aacggtgcgg tgcgtggcca gctggaggtt gcgctccgta gaagccacgc ttgccggaat    3000
caccctTgag ggaaactacg ccttcgatgc cgccgagggt ttcatcgcca gcaccggtgg    3060
ggatctccgt gacagttgtg gggatgttaa acactgccca gtgccagaaa ccagcgccgg    3120
ttggggcatc tgggtcgagg caggtgatcg cgagggattt g                        3161
```

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16

```
tcgagctcgg tacccttttt tggtctcgaa tgaca                               35
```

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17

```
catgctaaca gtactgttta ggtggcgtcc tcctc                               35
```

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18

```
cacctaaaca gtactgttag catgtgttct tatcg                               35
```

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19

```
ctcagaggat cccccccacc ggtgctggcg atga                                34
```

<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20

```
cgccacctaa acagtgaagc ctaaaaacga ccgag                               35
```

<210> SEQ ID NO 21
<211> LENGTH: 35
<212> TYPE: DNA
<213> ORGANISM: Artificial Sequence
<220> FEATURE:

<223> OTHER INFORMATION: primer

<400> SEQUENCE: 21
caaggttgta gtcatgttgt gtctcctcta aagat          35

<210> SEQ ID NO 22
<211> LENGTH: 35
<212> TYPE: DNA
<213> ORGANISM: Artificial Sequence
<220> FEATURE:
<223> OTHER INFORMATION: primer

<400> SEQUENCE: 22
tagaggagac acaacatgac tacaaccttg actcg          35

<210> SEQ ID NO 23
<211> LENGTH: 35
<212> TYPE: DNA
<213> ORGANISM: Artificial Sequence
<220> FEATURE:
<223> OTHER INFORMATION: primer

<400> SEQUENCE: 23
acacatgcta acagtcatgt cccagcgatg agtgc          35

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctggcggcga tttttcggtg          20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cgcgatcacc tgcctcgacc          20

<210> SEQ ID NO 26
<211> LENGTH: 5666
<212> TYPE: DNA
<213> ORGANISM: Corynebacterium glutamicum

<400> SEQUENCE: 26
tgtcatgctt ccggaggtgc cagggctcg agactccgga aagctatttg ccactccgat          60
gtttgggtca ctcgacgaga tacgtgctga tcacctaatt tggtgcacag ggtttcggcc         120
ggcgattagg ccagttcgtc aacttctcaa acacggacaa ccaaaggttc ctggtctttta        180 tttagtaggc tacggagatt ggacgggacc tgggtctgcg actatcacag gggtcgggct         240
ttatgccaag cgagcagcca aagagattgc cgcgtcagtc ggcaaagtcg ttaaatagtt         300
tgaaggctaa gaacttaatg ttaaagcgaa aattgttttg acacctcaac taatgcagcg         360
atgcgttctt tccagaatgc tttcatgaca gggatgctgt cttgatcagg caggcgtctg         420
tgctggatgc cgaagctgga tttattgtcg cctttggagg tgaagttgac gctcactcga         480
gaatcatcgg ccaaccattt ggcattgaat gttctaggtt cggaggcgga ggttttctca         540

```
attagtgcgg gatcgagcca ctgcgcccgc aggtcatcgt ctccgaagag cttccacact    600
ttttcgaccg gcaggttaag ggttttggag gcattggccg cgaacccatc gctggtcatc    660
ccgggtttgc gcatgccacg ttcgtattca taaccaatcg cgatgccttg agcccaccag    720
ccactgacat caaagttgtc cacgatgtgc tttgcgatgt gggtgtgagt ccaagaggtg    780
gcttttacgt cgtcaagcaa ttttagccac tcttcccacg gctttccggt gccgttgagg    840
atagcttcag gggacatgcc tggtgttgag ccttgcggag tggagtcagt catgcgaccg    900
agactagtgg cgctttgcct gtgttgctta ggcggcgttg aaaatgaact acgaatgaaa    960
agttcgggaa ttgtctaatc cgtactaagc tgtctacaca atgtctactt cagttacttc   1020
accagcccac aacaacgcac attcctccga attttggat gcgttggcaa accatgtgtt    1080
gatcggcgac ggcgccatgg gcacccagct ccaaggcttt gacctggacg tggaaaagga   1140
tttccttgat ctggaggggt gtaatgagat tctcaacgac acccgccctg atgtgttgag   1200
gcagattcac cgcgcctact ttgaggcggg agctgacttg gttgagacca atacttttgg   1260
ttgcaacctg ccgaacttgg cggattatga catcgctgat cgttgccgtg agcttgccta   1320
caagggcact gcagtggcta gggaagtggc tgatgagatg gggccgggcc gaaacggcat   1380
gcggcgtttc gtggttggtt ccctgggacc tggaacgaag cttccatcgc tgggccatgc   1440
accgtatgca gatttgcgtg gcactacaa ggaagcagcg cttggcatca tcgacggtgg   1500
tggcgatgcc ttttgattg agactgctca ggacttgctt caggtcaagg ctgcggttca    1560
cggcgttcaa gatgccatgg ctgaacttga tacattcttg cccattattt gccacgtcac   1620
cgtagagacc accggcacca tgctcatggg ttctgagatc ggtgccgcgt tgacagcgct   1680
gcagccactg ggtatcgaca tgattggtct gaactgcgcc accggcccag atgagatgag   1740
cgagcacctg cgttacctgt ccaagcacgc cgatattcct gtgtcggtga tgcctaacgc   1800
aggtcttcct gtcctgggta aaaacggtgc agaatacca cttgaggctg aggatttggc    1860
gcaggcgctg gctggattcg tctccgaata tggcctgtcc atggtgggtg ttgttgtgg    1920 caccacacct gagcacatcc gtgcggtccg cgatgcggtg gttggtgttc cagagcagga   1980
aacctccaca ctgaccaaga tccctgcagg ccctgttgag caggcctccc gcgaggtgga   2040
gaaagaggac tccgtcgcgt cgctgtacac ctcggtgcca ttgtcccagg aaaccggcat   2100
ttccatgatc ggtgagcgca ccaactccaa cggttccaag gcattccgtg aggcaatgct   2160
gtctggcgat tgggaaaagt gtgtggatat tgccaagcag caaacccgcg atggtgcaca   2220
catgctggat ctttgtgtgg attacgtggg acgagacggc accgccgata tggcgacctt   2280
ggcagcactt cttgctacca gctccacttt gccaatcatg attgactcca ccgagccaga   2340
ggttattcgc acaggccttg agcacttggg tggacgaagc atcgttaact ccgtcaactt   2400
tgaagacggc gatggccctg agtcccgcta ccagcgcatc atgaaactgg taaagcagca   2460
cggtgcggcc gtggttgcgc tgaccattga tgaggaaggc caggcacgta ccgctgagca   2520
caaggtgcgc attgctaaac gactgattga cgatatcacc ggcagctacg gcctggatat   2580
caaagacatc gttgtggact gcctgacctt cccgatctct actggccagg aagaaaccag   2640
gcgagatggc attgaaacca tcgaagccat ccgcagctct aagaagctct acccagaaat   2700
ccacaccacc ctgggtctgt ccaatatttc cttcggcctg aaccctgctg cacgccaggt   2760
tcttaactct gtgttcctca atgagtgcat tgaggctggt ctggactctg cgattgcgca   2820
cagctccaag attttgccga tgaaccgcat tgatgatcgc cagcgcgaag tggcgttgga   2880
```

```
tatggtctat gatcgccgca ccgaggatta cgatccgctg caggaattca tgcagctgtt    2940
tgagggcgtt tctgctgccg atgccaagga tgctcgcgct gaacagctgg ccgctatgcc    3000
tttgtttgag cgtttggcac agcgcatcat cgacggcgat aagaatggcc ttgaggatga    3060
tctggaagca ggcatgaagg agaagtctcc tattgcgatc atcaacgagg accttctcaa    3120
cggcatgaag accgtgggtg agctgtttgg ttccggacag atgcagctgc cattcgtgct    3180
gcaatcggca gaaaccatga aaactgcggt ggcctatttg gaaccgttca tggaagagga    3240
agcagaagct accggatctg cgcaggcaga gggcaagggc aaaatcgtcg tggccaccgt    3300
caagggtgac gtgcacgata tcggcaagaa cttggtggac atcatttttgt ccaacaacgg    3360
ttacgacgtg gtgaacttgg gcatcaagca gccactgtcc gccatgttgg aagcagcgga    3420
agaacacaaa gcagacgtca tcggcatgtc gggacttctt gtgaagtcca ccgtggtgat    3480
gaaggaaaac cttgaggaga tgaacaacgc cggcgcatcc aattacccag tcattttggg    3540
tggcgctgcg ctgacgcgta cctacgtgga aaacgatctc aacgaggtgt acaccggtga    3600
ggtgtactac gcccgtgatg ctttcgaggg cctgcgcctg atggatgagg tgatggcaga    3660
aaagcgtggt gaaggacttg atcccaactc accagaagct attgagcagg cgaagaagaa    3720
ggcggaacgt aaggctcgta atgagcgttc ccgcaagatt gccgcggagc gtaaagctaa    3780
tgcggctccc gtgattgttc cggagcgttc tgatgtctcc accgatactc caaccgcggc    3840
accaccgttc tggggaaccc gcattgtcaa gggtctgccc ttggcggagt tcttgggcaa    3900
ccttgatgag cgcgccttgt tcatggggca gtggggtctg aaatccaccc gcggcaacga    3960
gggtccaagc tatgaggatt tggtggaaac tgaaggccga ccacgcctgc gctactggct    4020
ggatcgcctg aagtctgagg gcattttgga ccacgtggcc ttggtgtatg gctacttccc    4080
agcggtcgcg gaaggcgatg acgtggtgat cttggaatcc ccggatccac acgcagccga    4140
acgcatgcgc tttagcttcc cacgccagca gcgcggcagg ttcttgtgca tcgcggattt    4200
cattcgccca cgcgagcaag ctgtcaagga cggccaagtg gacgtcatgc cattccagct    4260
ggtcaccatg ggtaatccta ttgctgattt cgccaacgag ttgttcgcag ccaatgaata    4320
ccgcgagtac ttggaagttc acggcatcgg cgtgcagctc accgaagcat ggccgagta    4380
ctggcactcc cgagtgcgca gcgaactcaa gctgaacgac ggtggatctg tcgctgattt    4440
tgatccagaa gacaagacca agttcttcga cctggattac cgcggcgccc gcttctcctt    4500
tggttacggt tcttgccctg atctggaaga ccgcgcaaag ctggtggaat tgctcgagcc    4560
aggccgtatc ggcgtggagt tgtccgagga actccagctg cacccagagc agtccacaga    4620
cgcgtttgtg ctctaccacc cagaggcaaa gtactttaac gtctaacacc tttgagaggg    4680
aaaactttcc cgcacattgc agatcgtgcc actttaacta aggttgacgg catgattaag    4740
gcgattttct gggacatgga cggcacgatg gtggactctg agccacagtg gggcattgct    4800
acctacgagc tcagcgaagc catgggccgc cgcctcaccc cggagctccg ggaactcacc    4860
gtcggctcga gcctgccgcg caccatgcgc ttatgcgcag agcacgcagg cattacattg    4920
agcgacgcgg actacgagcg ctaccgggct ggcatgttcg cccgggtcca tgagcttttc    4980
gacgaatccc tcgtcccaaa tccaggcgtc accgaactcc tgacagagtt gaaggccctc    5040
gagatcccca tgttggtcac caccaacaca gagcgcgatc tcgcgacccg ttcagtcgca    5100
gccgtgggaa atgagttctt catcggttct atcgctggtg atgaagtccc aacagcaaag    5160
ccagcccccg acatgtacct cgaagcagca cgacgtgtgg gctttgaccc atcagagtgc    5220
ctcgtgttcg aagattccta caacggcatg ctgggcgctg ttactgcagg ttgccgcgtc    5280
```

-continued

| | |
|---|---|
| attggtctgc acccagaaga agtccaagcg ccagaaggtg tagtgccttt gcgttccctc | 5340 |
| cacggtaaaa actctttcga aggtgtcacc gctgagatgg tcactgcctg gtaccaccag | 5400 |
| atcgagccgg caggtgtcgc aaaataaaac caggtggggg agtgaaatta ttcgactaat | 5460 |
| atcctccccc aaacacacat tgataactgt tgtgtggaag aatgtaccga gtgaagacat | 5520 |
| ttgactcgct gtacgaagaa cttcttaacc gtgctcagac ccgccctgaa gggtctggaa | 5580 |
| ccgtggccgc cttggataaa ggcatccatc atctaggtaa aaggtcatc gaagaagccg | 5640 |
| gagaggtctg gattgcagcc gagtat | 5666 |

<210> SEQ ID NO 27
<211> LENGTH: 3613
<212> TYPE: DNA
<213> ORGANISM: Corynebacterium glutamicum
<400> SEQUENCE: 27

| | |
|---|---|
| tcctgtgggg tgaacttgac ctgtgctggg ccacgacgtc cgaaaacgtg cacttcagtg | 60 |
| gccttgtttt ctttgaggga gtcgtagacg ttgtcggaaa tttcggtgac tttgagctcg | 120 |
| tcgcctgtct tagccaggat gcgggctacg tcgaggccga cgttaccaac gccgataaca | 180 |
| gcgacggact gtgcagacag atcccaggag cgctcgaagc gtgggttgcc gtcgtagaag | 240 |
| ccaacgaact cgccggcacc gaaggagcct tctgcttcaa ttccggggat gttgaggtcg | 300 |
| cggtctgcaa ctgcgccggt ggagaacacg actgcatcgt agtagtcgcg gagttcttcg | 360 |
| acggtgatgt ctttgccgat tcaatgtta ccgagcaggc gcaggcgtgg cttgtccaac | 420 |
| acgttgtgca gggacttaac gatgcccttg atgcgtgggt ggtctggagc aacgccgtaa | 480 |
| cggatgagtc cgaacggtgc aggcatttgc tcgaaaaggt caacgaacac ttcgcgctct | 540 |
| tcattgcgga tgaggaggtc ggatgcgtaa atgccagcag gccagctcc gatgacggct | 600 |
| acgcgcaggg gagttgtcat gtgtttgaag ttgccttcg tgagcccttt tatggaaaca | 660 |
| agggtgtgaa aatcaagtag ttaaaggtgt ttcaagtcca ggctgtttaa cactcctaga | 720 |
| ccgcttggtc tgtaaacgta gcagcgaaat gcgacaatgc gaagactttt gcttaattaa | 780 |
| attcaaactc catgaaaaaa ctagacagat cggtctatta tattcacggt gaacctaacc | 840 |
| taatatcccc aggttaattc atttaaacgg gcattaggtg actccattgc tttcagtctc | 900 |
| atgaatctaa tggttggtct agacagagcg gtacgtctaa gtttgcggat agatcaaacc | 960 |
| gagtgacatg tacttcacta gctctttaag gattaactcc ccatgacaac aaccaccgga | 1020 |
| agtgcccggc cagcacgtgc cgccaggaag cctaagcccg aaggccaatg gaaaatcgac | 1080 |
| ggcaccgagc cgcttaacca tgccgaggaa attaagcaag aagaaccgc ttttgctgtc | 1140 |
| aagcagcggg tcattgatat ttactccaag cagggttttt cttccattgc accggatgac | 1200 |
| attgccccac gctttaagtg gttgggcatt tacacccagc gtaagcagga tctgggcggt | 1260 |
| gaactgaccg gtcagcttcc tgatgatgag ctgcaggatg agtacttcat gatgcgtgtg | 1320 |
| cgttttgatg gcggactggc ttcccctgag cgcctgcgtg ccgtgggtga aatttctagg | 1380 |
| gattatgctc gttccaccgc ggacttcacc gaccgccaga acattcagct gcactggatt | 1440 |
| cgtattgaag atgtgcctgc gatctgggag aagctagaaa ccgtcggact gtccaccatg | 1500 |
| cttggttgcg gtgacgttcc acgtgttatc ttgggctccc cagtttctgg cgtagctgct | 1560 |
| gaagagctga tcgatgccac cccggctatc gatgcgattc gtgagcgcta cctagacaag | 1620 |
| gaagagttcc acaaccttcc tcgtaagttt aagactgcta tcactggcaa ccagcgccag | 1680 |

```
gatgttaccc acgaaatcca ggacgtttcc ttcgttcctt cgattcaccc agaattcggc    1740
ccaggatttg agtgctttgt gggcggtggc ctgtccacca acccaatgct tgctcagcca    1800
cttggttctt ggattccact tgatgaggtt ccagaagtgt gggctggcgt cgccggaatt    1860
ttccgcgact acggcttccg acgcctgcgt aaccgtgctc gcctcaagtt cttggtggca    1920
cagtggggta ttgagaagtt ccgtgaagtt cttgagaccg aatacctcga gcgcaagctg    1980
atcgatggcc cagttgttac caccaaccct ggctaccgtg accacattgg cattcaccca    2040
caaaaggacg gcaagttcta cctcggtgtg aagccaaccg ttggacacac caccggtgag    2100
cagctcattg ccattgctga tgttgcagaa aagcacggca tcaccaggat cgtaccacg     2160
gcggaaaagg aactgctctt cctcgatatt gagagaaaga accttactac cgttgcacgc    2220
gacctggatg aaatcggact gtactcttca ccttccgagt ccgccgcgg catcatttcc     2280
tgcaccggct tggagttctg caagcttgcg cacgcaacca ccaagtcacg agcaattgag    2340
cttgtcgacg aactggaaga gcgcctcggc gatttggatg ttcccatcaa gattgcactg    2400
aacggttgcc ctaactcttg tgcacgcacc caggtttccg acatcggatt caagggacag    2460
accgtcactg atgctgacgg caaccgcgtt gaaggtttcc aggttcacct gggcggttcc    2520
atgaacttgg atccaaactt cggacgcaag ctcaagggcc acaaggttat tgccgatgaa    2580
gtggagagt acgtcactcg cgttgttacc cacttcaagg aacagcgcca cgaggacgag     2640
cacttccgcg attgggtcca gcgggccgct gaggaagatt tggtgtgagt cttcggagga    2700
aacccaatcc caaccgcaac caccctctgt actgcccata ctgcgcggga gaagttcttt    2760
tccccgatga gcaaacagaa ttcgcgtggt tgtgtgcgga ttgcaccaga gtttttgaag    2820
tgaaatatca cggccaggac gatccagtgc acaggccagc accagcaaag tccacatcgc    2880
aagcattaaa agaatctctc gaaagacaca aaagaggtga gtcgcaacaa tgagcttca    2940
actagttaac gccctgaaaa atactggttc ggtaaaagat cccgagatct caccccgaagg   3000
acctcgcacg accacaccgt tgtcaccaga ggtagcaaaa cataacgagg aactcgtcga    3060
aaagcatgct gctgcgttgt atgacgccag cgcgcaagag atcctggaat ggacagccga    3120
gcacgcgccg ggcgctattg cagtgacctt gagcatggaa acaccgtgc tggcggagct     3180
ggctgcgcgg cacctgccgg aagctgattt cctcttttg gacaccggtt accacttcaa    3240
ggagacccctt gaagttgccc gtcaggtaga tgagcgctat tcccagaagc ttgtcaccgc   3300
gctgccgatc ctcaagcgca cggagcagga ttccatttat ggtctcaacc tgtaccgcag    3360
caacccagcg cgtgctgcc gaatgcgcaa agttgaaccg ctggcggcgt cgttaagccc     3420
atacgctggc tggatcaccg gcctgcgccg cgctgatggc ccaacccgtg ctcaagcccc    3480
tgcgctgagc ttggatgcca ccggcaggct caagatttct ccaattatca cctggtcatt    3540
ggaggaaacc aacgagttca ttgcggacaa caacctcatc gatcacccac ttacccatca    3600
gggttatcca tca                                                       3613
```

<210> SEQ ID NO 28
<211> LENGTH: 3311
<212> TYPE: DNA
<213> ORGANISM: Corynebacterium glutamicum

<400> SEQUENCE: 28

```
ctcattccag cgtcacgacg ttccgaaggt actggttacc tggcattggg cactaccgtt      60
tctgcagcac ttggaccagc cctagcactt tttgtcctag aacatttga ttcgacatg       120
ctgtttatcg tggtcttggc aacctcggtc atctctttga tcgccgtcgt gttcatgtac     180
```

-continued

```
tttaagacca gcgaccctga gccttctggg gaaccagcca agttcagctt caaatctatt    240
atgaacccaa agatcatccc catcggcatc tttatcttgc ttatttgctt tgcttactct    300
ggcgtcattg cctacatcaa cgcatttgct gaagaacgcg atctgattac gggtgctgga    360
ttgttcttca ttgcctacgc agtatcaatg tttgtgatgc gcagcttcct tggcaaactg    420
caggaccgtc gcggagacaa cgtcgttatt tactttggat tgttcttctt cgttatttcc    480
ttgacgattt tgtcctttgc cacttccaac tggcacgttg tgttgtccgg agtcattgca    540
ggtctgggat acggcacttt gatgccagca gtgcagtcca tcgctgttgg tgtagtagac    600
aaaaccgaat tcggtacggc cttctccact tgttcctgt tgtggactt aggttttggc     660 tttggaccta ttatcctggg agcagtttct gcggcaattg gtttcggacc tatgtatgca    720
gcactggcag gtgtgggtgt gattgccgga atcttctacc tgttcacaca cgctcgcacc    780
gatcgagcta agaatggctt tgttaaacac ccagagcctg tcgctttagt tagctagttc    840
tttcagcttt ccctcccgat cagcgtaaac cggcccttcc ggttttgggg tacatcacag    900
aacctgggct agcggtgtag acccgaaaat aaacgagcct tttgtcaggg ttaaggttta    960
ggtatctaag ctaaccaaac accaacaaaa ggctctaccc atgaagtcta ccggcaacat   1020
catcgctgac accatctgcc gcactgcgga actaggactc accatcaccg gcgcttccga   1080
tgcaggtgat tacaccctga tcgaagcaga cgcactcgac tacacctcca cctgcccaga   1140
atgctcccaa cctggggtgt tcgtcatca cacccaccgg atgctcattg atttacccat    1200
cgtcgggttt cccaccaaac tgtttatccg tctacctcgc taccgctgca ccaaccccac   1260
atgtaagcaa aagtatttcc aagcagaact aagctgcgct gaccacggta aaaggtcac    1320 ccaccgggtc acccgctgga ttttacaacg ccttgctatt gaccggatga gtgttcacgc   1380
aaccgcgaaa gcacttgggc tagggtggga tttaacctgc caactagccc tcgatatgtg   1440
ccgtgagctg gtctataacg atcctcacca tcttgatgga gtgtatgtca ttggggtgga   1500
tgagcataag tggtcacata atagggctaa gcatggtgat gggtttgtca ccgtgattgt   1560
cgatatgacc gggcatcggt atgactcacg gtgtcctgcc cggttattag atgtcgtccc   1620
aggtcgtagt gctgatgctt tacggtcctg gcttggctcc cgcggtgaac agttccgcaa   1680
tcagatacgg atcgtgtcca tggatggatt ccaaggctac gccacagcaa gtaaagaact   1740
cattccttct gctcgtcgcg tgatggatcc attccatgtt gtgcggcttg ctggtgacaa   1800
gctcaccgcc tgccggcaac gcctccagcg ggagaaatac cagcgtcgtg gtttaagcca   1860
ggatccgttg tataaaaacc ggaagacctt gttgaccacg cacaagtggt tgagtcctcg   1920
tcagcaagaa agcttggagc agttgtgggc gtatgacaaa gactacgggg cgttaaagct   1980
tgcgtggctt gcgtatcagg cgattattga ttgttatcag atgggtaata agcgtgaagc   2040
gaagaagaaa atgcggacca ttattgatca gcttcgggtg ttgaaggggc gaataagga    2100 actcgcgcag ttgggtcgta gtttgtttaa acgacttggt gatgtgttgg cgtatttcga   2160
tgttggtgtc tccaacggtc cggtcgaagc gatcaacgga cggttggagc atttgcgtgg   2220
gattgctcta ggtttccgta atttgaacca ctacattctg cggtgcctta tccattcagg   2280
gcagttggtc cataagatca atgcactcta aaacaggaag agcccgtaaa cctctgacta   2340
gcgtcaccct ctgattaagg cgaccgcgga tttaagagca gaggctgcca cgagcgcatc   2400
ttcacggctg tgtgttgtac taaaagtaca gcgcacagcc gttcgtgctt gatcctcctc   2460
aagccccaac gccagcaaca catgggatac ctctccggaa ccacaggcag aaccagggga   2520
```

-continued

| | |
|---|---|
| gcacacaatg ccttggcgtt ccaattccag aagaacagtt tcagatccta tgctgtcgaa | 2580 |
| gagaaaagat gcgtgtccat caatgcgcat cctaggatgt ccagtcaggt gtgctcccgg | 2640 |
| gatagtgaga acttcctcga tgaattcgcc aagatctgga taggattccg ccctggccaa | 2700 |
| ttccaaggca gtggcaaagg cgatagcccc cgcaacgttt tccgtgccac tacgccgccc | 2760 |
| ttttcctgg ccgccgccat ggattaccgg ctccagggga agctttgacc ataacactcc | 2820 |
| aatccctta ggcgcaccga atttatgacc cgacaaactt aacgcgtcaa ctcccaagtc | 2880 |
| aaaggttaaa tgtgcagctt gcactgcatc ggtgtgaaaa ggcgtactgc ttaccgccgc | 2940 |
| caactcagct atcggctgaa tggttcccac ctcattgttg cataaccaa tgctgatcaa | 3000 |
| tgtggtgtcc ggcctgactg ctttgcggag accctccggg gagatcagcc cagtgtgatc | 3060 |
| gggggatagg taggtgatct cgaaatcatg aaacctttca agataagcag cagtttctag | 3120 |
| gacactgtca tgctcgatcg gggtggtgat gaggtgccgg ccacgaggat tagctaagca | 3180 |
| cgctcctttg atagcgaggt tgttggcttc tgatccaccc gacgtaaacg tcacctgtgt | 3240 |
| ggggcgtcct ccgataatgc gggccacccg agttcgagca tcctccagcc ccgcagaggc | 3300 |
| gagtcttccc a | 3311 |

<210> SEQ ID NO 29
<211> LENGTH: 35
<212> TYPE: DNA
<213> ORGANISM: Artificial Sequence
<220> FEATURE:
<223> OTHER INFORMATION: primer

<400> SEQUENCE: 29

| | |
|---|---|
| acccggggat cctctagaat gtttgtgatg cgcag | 35 |

<210> SEQ ID NO 30
<211> LENGTH: 35
<212> TYPE: DNA
<213> ORGANISM: Artificial Sequence
<220> FEATURE:
<223> OTHER INFORMATION: primer

<400> SEQUENCE: 30

| | |
|---|---|
| gtcagagagt acttacgctg atcgggaggg aaagc | 35 |

<210> SEQ ID NO 31
<211> LENGTH: 35
<212> TYPE: DNA
<213> ORGANISM: Artificial Sequence
<220> FEATURE:
<223> OTHER INFORMATION: primer

<400> SEQUENCE: 31

| | |
|---|---|
| atcagcgtaa gtactctctg actagcgtca ccctc | 35 |

<210> SEQ ID NO 32
<211> LENGTH: 35
<212> TYPE: DNA
<213> ORGANISM: Artificial Sequence
<220> FEATURE:
<223> OTHER INFORMATION: primer

<400> SEQUENCE: 32

| | |
|---|---|
| ctgcaggtcg actctagaaa agggattgga gtgtt | 35 |

<210> SEQ ID NO 33
<211> LENGTH: 35

```
<212> TYPE: DNA
<213> ORGANISM: Artificial Sequence
<220> FEATURE:
<223> OTHER INFORMATION: primer

<400> SEQUENCE: 33
caacgaaagg aaacaatgtc tacttcagtt acttc                              35

<210> SEQ ID NO 34
<211> LENGTH: 35
<212> TYPE: DNA
<213> ORGANISM: Artificial Sequence
<220> FEATURE:
<223> OTHER INFORMATION: primer

<400> SEQUENCE: 34
tagtcagaga gtgatttaga cgttaaagta ctttg                              35

<210> SEQ ID NO 35
<211> LENGTH: 35
<212> TYPE: DNA
<213> ORGANISM: Artificial Sequence
<220> FEATURE:
<223> OTHER INFORMATION: primer

<400> SEQUENCE: 35
atcaaaacag atatcatgac aacaaccacc ggaag                              35

<210> SEQ ID NO 36
<211> LENGTH: 35
<212> TYPE: DNA
<213> ORGANISM: Artificial Sequence
<220> FEATURE:
<223> OTHER INFORMATION: primer

<400> SEQUENCE: 36
cgctagtcag agagttcaca ccaaatcttc ctcag                              35

<210> SEQ ID NO 37
<211> LENGTH: 35
<212> TYPE: DNA
<213> ORGANISM: Artificial Sequence
<220> FEATURE:
<223> OTHER INFORMATION: primer

<400> SEQUENCE: 37
ccgatcagcg taagtagaaa catcccagcg ctact                              35

<210> SEQ ID NO 38
<211> LENGTH: 35
<212> TYPE: DNA
<213> ORGANISM: Artificial Sequence
<220> FEATURE:
<223> OTHER INFORMATION: primer

<400> SEQUENCE: 38
aactgaagta gacattgttt cctttcgttg ggtac                              35

<210> SEQ ID NO 39
<211> LENGTH: 35
<212> TYPE: DNA
<213> ORGANISM: Artificial Sequence
<220> FEATURE:
<223> OTHER INFORMATION: primer

<400> SEQUENCE: 39
```

```
tactttaacg tctaaggtac cggcgcttca tgtca                                    35
```

<210> SEQ ID NO 40
<211> LENGTH: 35
<212> TYPE: DNA
<213> ORGANISM: Artificial Sequence
<220> FEATURE:
<223> OTHER INFORMATION: primer

<400> SEQUENCE: 40

```
ggtggttgtt gtcatgatat ctgttttgat ctcct                                    35
```

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41

```
atccccatcg gcatctttat                                                     20
```

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42

```
cgatcacact gggctgatct                                                     20
```

<210> SEQ ID NO 43
<211> LENGTH: 319
<212> TYPE: PRT
<213> ORGANISM: Corynebacterium glutamicum

<400> SEQUENCE: 43

```
Met Lys Phe Lys Lys Ile Ala Leu Val Leu Ala Phe Gly Leu Gly Leu
1               5                   10                  15

Ala Ser Cys Ser Ser Ala Ser Gly Asp Pro Ala Thr Asn Ala Asp Gly
            20                  25                  30

Ser Ile Asp Leu Ser Lys Val Thr Leu Asn Ile Gly Asp Gln Ile Ala
        35                  40                  45

Gly Thr Glu Gln Val Leu Gln Ala Ser Gly Glu Leu Asp Asp Val Pro
    50                  55                  60

Tyr Lys Ile Glu Trp Ser Ser Phe Thr Ser Gly Pro Pro Gln Ile Glu
65                  70                  75                  80

Ala Leu Asn Ala Gly Gln Ile Asp Phe Ala Ile Thr Gly Asn Thr Pro
                85                  90                  95

Pro Ile Ile Gly Gly Pro Thr Asn Thr Lys Val Val Ser Ala Tyr Asn
            100                 105                 110

Asn Asp Ala Leu Gly Asp Val Ile Leu Val Ala Pro Asp Ser Ser Ile
        115                 120                 125

Thr Ser Val Ala Asp Leu Ala Gly Lys Lys Val Ala Val Ala Arg Gly
    130                 135                 140

Ser Ser Ala His Gly His Leu Ile Gln Gln Leu Glu Lys Ala Gly Val
145                 150                 155                 160

Ser Val Asp Asp Val Glu Ile Asn Leu Leu Gln Pro Ser Asp Ala Lys
                165                 170                 175
```

```
Ala Ala Phe Gln Asn Gly Gln Val Asp Ala Trp Ala Val Trp Asp Pro
            180                 185                 190

Tyr Ser Ser Gln Ala Glu Leu Glu Gly Ala Gln Val Leu Val Arg Gly
        195                 200                 205

Ala Gly Leu Val Ser Gly His Gly Phe Gly Val Ala Ser Asp Glu Ala
    210                 215                 220

Leu Asp Asp Pro Ala Lys Glu Ala Ala Leu Ala Asp Phe Leu Asp Arg
225                 230                 235                 240

Val Ala Asp Ser Tyr Glu Trp Ala Glu Asp Asn Thr Asp Glu Trp Ala
                245                 250                 255

Thr Ile Phe Ser Gln Glu Ser Gly Phe Asp Pro Glu Ala Ser Gln Leu
            260                 265                 270

Asn Thr Arg Ser Leu Arg His Gln Val Pro Leu Asp Glu Ser Val Asn
        275                 280                 285

Thr Tyr Gln Asn Ala Leu Ile Asp Ala Phe Val Ser Ala Gly Leu Val
    290                 295                 300

Glu Asp Phe Asn Phe Glu Asp Thr Val Asp Thr Arg Phe Glu Gly
305                 310                 315

<210> SEQ ID NO 44
<211> LENGTH: 243
<212> TYPE: PRT
<213> ORGANISM: Corynebacterium glutamicum

<400> SEQUENCE: 44

Met Thr Ala Thr Leu Ser Leu Lys Pro Ala Ala Thr Val Arg Gly Leu
1               5                   10                  15

Arg Lys Ser Tyr Gly Thr Lys Glu Val Leu Gln Gly Ile Asp Leu Thr
            20                  25                  30

Ile Asn Cys Gly Glu Val Thr Ala Leu Ile Gly Arg Ser Gly Ser Gly
        35                  40                  45

Lys Ser Thr Ile Leu Arg Val Leu Ala Gly Leu Ser Lys Glu His Ser
50                  55                  60

Gly Ser Val Glu Ile Ser Gly Asn Pro Ala Val Ala Phe Gln Glu Pro
65                  70                  75                  80

Arg Leu Leu Pro Trp Lys Thr Val Leu Asp Asn Val Thr Phe Gly Leu
                85                  90                  95

Asn Arg Thr Asp Ile Ser Trp Ser Glu Ala Gln Glu Arg Ala Ser Ala
            100                 105                 110

Leu Leu Ala Glu Val Lys Leu Pro Asp Ser Asp Ala Ala Trp Pro Leu
        115                 120                 125

Thr Leu Ser Gly Gly Gln Ala Gln Arg Val Ser Leu Ala Arg Ala Leu
    130                 135                 140

Ile Ser Glu Pro Glu Leu Leu Leu Leu Asp Glu Pro Phe Gly Ala Leu
145                 150                 155                 160

Asp Ala Leu Thr Arg Leu Thr Ala Gln Asp Leu Leu Leu Lys Thr Val
                165                 170                 175

Asn Thr Arg Asn Leu Gly Val Leu Leu Val Thr His Asp Val Ser Glu
            180                 185                 190

Ala Ile Ala Leu Ala Asp His Val Leu Leu Asp Asp Gly Ala Ile
        195                 200                 205

Thr His Ser Leu Thr Val Asp Ile Pro Gly Asp Arg Arg Thr His Pro
    210                 215                 220

Ser Phe Ala Ser Tyr Thr Ala Gln Leu Leu Glu Trp Leu Glu Ile Thr
225                 230                 235                 240
```

Thr Pro Ala

<210> SEQ ID NO 45
<211> LENGTH: 256
<212> TYPE: PRT
<213> ORGANISM: Corynebacterium glutamicum

<400> SEQUENCE: 45

Met Thr Thr Thr Leu Thr Arg Pro Lys Ile Ala Leu Pro Ala Arg Ile
1               5                   10                  15

Tyr Ser Pro Leu Ala Val Leu Val Phe Trp Gln Leu Gly Ser Ser Leu
            20                  25                  30

Gly Ala Ile Pro Glu Arg Ile Leu Pro Ala Pro Thr Thr Ile Leu Ala
        35                  40                  45

Ala Ser Trp Glu Val Ala Thr Asn Gly Thr Leu Leu Asp Ala Leu Leu
    50                  55                  60

Val Ser Ser Gln Arg Val Leu Leu Gly Phe Ala Leu Gly Ala Val Leu
65                  70                  75                  80

Gly Ile Ser Leu Gly Val Leu Thr Gly Met Ser Arg Phe Ala Asp Thr
                85                  90                  95

Ala Val Asp Pro Leu Ile Gln Ala Ala Arg Ala Leu Pro His Leu Gly
            100                 105                 110

Leu Val Pro Leu Phe Ile Ile Trp Phe Gly Ile Gly Glu Leu Pro Lys
            115                 120                 125

Val Leu Ile Ile Ser Leu Gly Val Leu Tyr Pro Leu Tyr Leu Asn Thr
130                 135                 140

Ala Ser Gly Phe Arg Gln Ile Asp Pro Lys Leu Leu Glu Ala Gly His
145                 150                 155                 160

Val Met Gly Phe Gly Phe Phe Gln Arg Leu Arg Thr Ile Ile Ile Pro
                165                 170                 175

Ser Ala Ala Pro Gln Leu Phe Val Gly Leu Arg Gln Ala Ser Ala Ala
            180                 185                 190

Ala Trp Leu Ser Leu Ile Val Ala Glu Gln Val Asn Ala Arg Glu Gly
        195                 200                 205

Leu Gly Phe Leu Ile Asn Asn Ala Arg Asp Phe Tyr Arg Thr Asp Leu
    210                 215                 220

Val Ile Phe Gly Leu Ile Val Tyr Ala Ser Leu Gly Leu Leu Ser Glu
225                 230                 235                 240

Ala Leu Ile Arg Ala Trp Glu Arg His Thr Phe Arg Tyr Arg Asn Ala
                245                 250                 255